US012653952B2

(12) United States Patent
Langley et al.

(10) Patent No.: US 12,653,952 B2
(45) Date of Patent: Jun. 16, 2026

(54) DOSE DELIVERY DEVICE FIXTURE FOR TESTING SYSTEM AND METHODS THEREFOR

(71) Applicant: Regeneron Pharmaceuticals, Inc., Tarrytown, NY (US)

(72) Inventors: Trevor Langley, Rensselaer, NY (US); Elizabeth Hanchar, East Greenbush, NY (US); Wesley Mahunik, Rensselaer, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 762 days.

(21) Appl. No.: 18/062,622

(22) Filed: Dec. 7, 2022

(65) Prior Publication Data

US 2023/0173177 A1     Jun. 8, 2023

Related U.S. Application Data

(60) Provisional application No. 63/287,500, filed on Dec. 8, 2021.

(51) Int. Cl.
| | |
|---|---|
| *A61M 5/19* | (2006.01) |
| *A61M 5/315* | (2006.01) |
| *A61M 5/32* | (2006.01) |

(52) U.S. Cl.
CPC .......... *A61M 5/19* (2013.01); *A61M 5/31528* (2013.01); *A61M 5/3202* (2013.01)

(58) Field of Classification Search
CPC .. A61M 5/19; A61M 5/31528; A61M 5/3202; A61M 5/008; A61M 5/24; A61M 2209/02; A61M 2209/084
See application file for complete search history.

(56) References Cited

U.S. PATENT DOCUMENTS

| | | | |
|---|---|---|---|
| 8,672,881 B2 * | 3/2014 | Nagamatsu | ....... A61M 25/1002 604/97.02 |
| 11,241,330 B1 * | 2/2022 | Sabir | .................. A61B 18/0218 |
| 2009/0241644 A1 | 10/2009 | Bonfiglioli | |

FOREIGN PATENT DOCUMENTS

| | | |
|---|---|---|
| CN | 101216365 B | 12/2010 |
| CN | 206847862 U | 1/2018 |

(Continued)

OTHER PUBLICATIONS

International Search Report and Written Opinion mailed Mar. 16, 2023 in International Application No. PCT/US2022/081064 (13 pages).

(Continued)

*Primary Examiner* — Stephen D Meier
*Assistant Examiner* — Quang X Nguyen
(74) *Attorney, Agent, or Firm* — Bookoff McAndrews, PLLC

(57) ABSTRACT

A syringe fixture for holding a syringe in a test system, the fixture comprising a main housing comprising a first chamber, a second chamber, and an opening extending from the first chamber to the second chamber, wherein the first chamber comprises a first plurality of walls and a second plurality of walls forming a housing for at least a needle of the syringe, wherein the second chamber is configured to hold at least a flange portion of the syringe and the second chamber comprises a cover to enclose at least the flange portion of the syringe; and a base portion having a support, wherein the base portion is configured to receive a portion of a plunger rod, and wherein the base portion includes at least one geometric feature configured to allow or impart a rotational motion on the portion of the plunger rod received in the base portion.

20 Claims, 28 Drawing Sheets

(56)     References Cited

FOREIGN PATENT DOCUMENTS

| WO | 2019/118588 A1 | 6/2019 |
| WO | 2020/169824 A1 | 8/2020 |
| WO | 2020/247686 A1 | 12/2020 |

OTHER PUBLICATIONS

Design U.S. Appl. No. 29/760,798, filed Dec. 3, 2020 (38 pages).
Design U.S. Appl. No. 29/760,796, filed Dec. 3, 2020 (38 pages).
Instron® Universal Testing Systems, <www.instron.com/en-us/products/testing-systems/universal-testing-systems>, accessed Dec. 1, 2022 (9 pages).

* cited by examiner

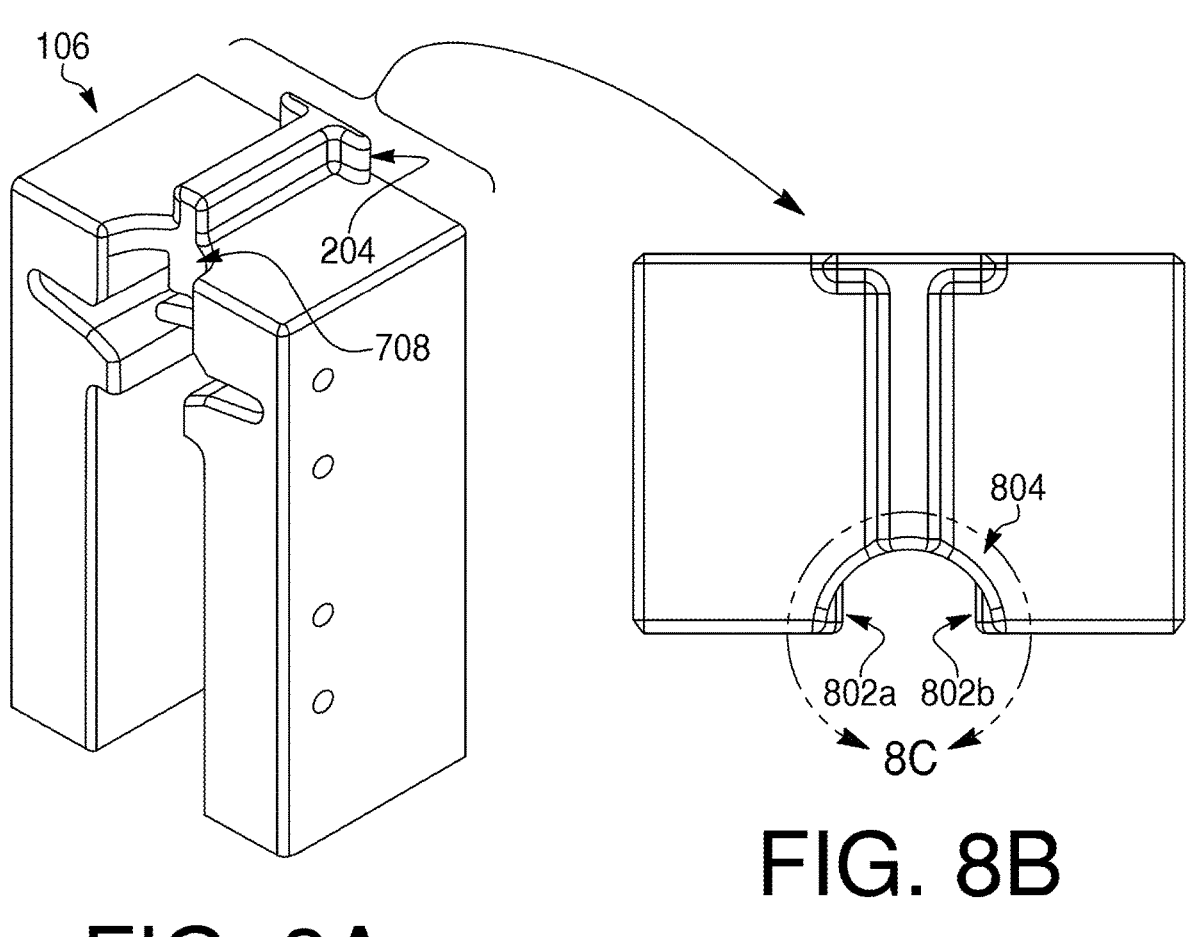
FIG. 8A
FIG. 8B
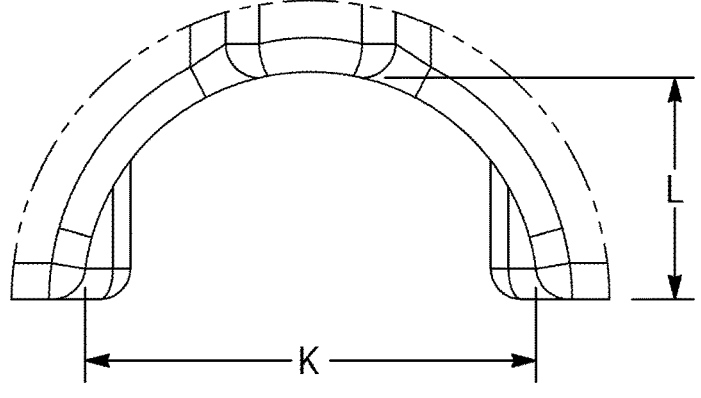
FIG. 8C

|          | Break Force | Snap Deflection Force | Air Glide Force | Fluid Priming Glide Force | Fluid Dosing Glide Force | Maximum Injection Force |
|----------|-------------|-----------------------|-----------------|---------------------------|--------------------------|-------------------------|
| Mean     | 2.956N      | 5.354N                | 2.6235N         | 12.885N                   | 15.508N                  | 15.997N                 |
| Std. Dev.| 0.609N      | 0.712N                | 0.4626N         | 3.759N                    | 1.545N                   | 1.573N                  |

| | Break Force | Snap Deflection Force | Air Glide Force | Fluid Priming Glide Force | Fluid Dosing Glide Force | Maximum Injection Force |
|---|---|---|---|---|---|---|
| Mean | 2.803N | 6.530N | 3.824N | 15.591N | 16.137N | 17.378N |
| Std. Dev. | 0.621N | 0.274N | 0.396N | 1.466N | 1.731N | 2.547N |

DOSE DELIVERY DEVICE FIXTURE FOR TESTING SYSTEM AND METHODS THEREFOR

This application claims the benefit of priority from U.S. Provisional Application No. 63/287,500, filed on Dec. 8, 2021, the entirety of which is incorporated herein by reference.

TECHNICAL FIELD

This disclosure is directed to a drug delivery device (e.g., syringes) fixture for a testing system and uses thereof.

INTRODUCTION

Mechanical test systems, such as tensile and compression test systems, are used in laboratory settings to perform real time analyses. Examples of such devices are the Instron® Low Force Universal Testing Systems and Instron® High Force Universal Testing Systems. (Instron, www.instron.com/en-us/products/testing-systems/universal-testing-systems, incorporated by reference herein). While such mechanical testing systems provide many beneficial uses, they are large and expensive instruments that are not easily adaptable to analyze a wide variety of devices. Additional components for the test system need to be obtained in order to properly hold a device (e.g., a syringe, an auto-injector, or other suitable drug delivery devices) of interest, so that the test system may accurately analyze the functional forces of such device. Depending on components, size, and/or configuration of the device, it may be difficult to properly secure a device within the test system so that accurate tests and measurements may be obtained. Even minor disturbances may impact the results produced from a test system. For example, incorrect alignment of the device within the test system may affect the results. Test systems should be configured to properly hold and support the device of interest to ensure accurate testing and analysis.

SUMMARY OF THE DISCLOSURE

In one aspect, the present disclosure describes a syringe fixture for holding a syringe in a test system, the fixture comprising a main housing comprising a first chamber, a second chamber, and an opening extending from the first chamber to the second chamber, wherein the first chamber comprises a first plurality of walls having a first length and a second plurality of walls having a second length, wherein the second length is less than the first length, and the first and second pluralities of walls form a housing for at least a needle of the syringe, and wherein the second chamber is configured to hold at least a flange portion of the syringe and the second chamber comprises a cover to enclose at least the flange portion of the syringe; and a base portion having a support, wherein the base portion is configured to receive a portion of a plunger rod of the syringe, and wherein the base portion includes at least one geometric feature configured to allow or impart a rotational motion on the portion of the plunger rod received in the base portion.

Various embodiments of the syringe fixture may include one or more of the following aspects. The base portion may include a holder for a plunger rod of the syringe and a casing, wherein the casing and the holder may be configured to be secured together via a fastener to support the plunger rod. The base portion may include a lug configured to receive a plunger rod of the syringe and a connector, wherein the lug and connector may be secured together to support the plunger rod. The second chamber may be removable from the main housing. The second chamber may have a first configuration and may be interchangeable with a different second chamber having a second configuration, wherein the second configuration is different from the first configuration. The second plurality of walls may include a top wall and a bottom wall, the top wall comprising a fastener for securing the main housing to the test system. The support of the base portion may include screw holes for securing the base to the test system. The cover may be attached to the second chamber via hinges and a closure, the closure configured to allow for opening and closing of the cover. The second chamber may include a chamber extension extending from a bottom section of the second chamber and the cover may include a cover extension extending from a bottom section of the cover, wherein each portion may have a height ranging from about 4.80 mm to about 5.20 mm. Each of the chamber extension of the second chamber and the cover extension of the cover may have a length ranging from about 13.22 mm to about 13.62 mm. A clearance between the chamber extension of the second chamber and the cover extension of the cover may range from about 12.95 mm to about 13.35 mm. The first chamber of the main housing may be configured to be secured to a movable portion of the test system and the support of the base portion may be configured to be secured to a stationary portion of the test system. The first chamber of the main housing may be configured to be secured to a stationary portion of the test system and the support of the base portion may be configured to be secured to a movable portion of the test system.

In another aspect, the present disclosure describes a syringe fixture for holding a syringe in a test system, the fixture comprising a main housing comprising a first chamber, a second chamber, and an opening extending from the first chamber to the second chamber, wherein the first chamber comprises a housing for at least a needle of the syringe, and wherein the second chamber is configured to receive at least a flange portion of the syringe and the second chamber comprises a cover to enclose at least the flange portion of the syringe; and a base portion having a support, wherein the base portion includes a lug configured to receive a: plunger rod of the syringe, and a connector, wherein the lug and connector are secured together to support the plunger rod.

Various embodiments of the syringe fixture may include one or more of the following aspects. The base portion may include a thumb nut to secure and stabilize the lug and connector to the test system. The lug may include an opening for receiving a portion of the plunger rod, and wherein the opening may include a plurality of ridges configured to engage with a portion of the plunger rod. The lug may include a first end having a first diameter and a second end having a second diameter, wherein the second diameter is larger than the first diameter, and a sidewall extending from the first end to the second end, wherein the sidewall flares outwardly from the first end to the second end.

In another aspect, the present disclosure describes a method for testing a syringe, the method comprising securing a syringe fixture to a test system, the fixture comprising a main housing comprising a first chamber, a second chamber, and an opening extending from the first chamber to the second chamber, wherein the first chamber comprises a housing for at least a needle and a needle cap of the syringe, and wherein the second chamber is configured to hold at least a flange portion of the syringe and the second chamber comprises a cover to enclose at least the flange portion of the syringe; and a base portion having a support, and inserting the syringe into the syringe fixture. Various methods of the present disclosure may further comprise securing the first chamber of the main housing to a movable portion of the test system and securing the support of the base portion to a stationary portion of the test system, or may further comprise securing the first chamber of the main housing to a stationary portion of the test system and securing the support of the base portion to a movable portion of the test system.

BRIEF DESCRIPTION OF THE FIGURES

The accompanying drawings, which are incorporated in and constitute a part of this specification, illustrate various examples and, together with the description, serve to explain the principles of the disclosed examples and embodiments.

Aspects of the disclosure may be implemented in connection with embodiments illustrated in the attached drawings. These drawings show different aspects of the present disclosure and, where appropriate, reference numerals illustrating like structures, components, materials, and/or elements in different figures are labeled similarly. It is understood that various combinations of the structures, components, and/or elements, other than those specifically shown, are contemplated and are within the scope of the present disclosure.

Moreover, there are many embodiments described and illustrated herein. The present disclosure is neither limited to any single aspect or embodiment thereof, nor is it limited to any combinations and/or permutations of such aspects and/or embodiments. Moreover, each of the aspects of the present disclosure, and/or embodiments thereof, may be employed alone or in combination with one or more of the other aspects of the present disclosure and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended to reflect or indicate the embodiment(s) is/are "example" embodiment(s).

Figure 1A:
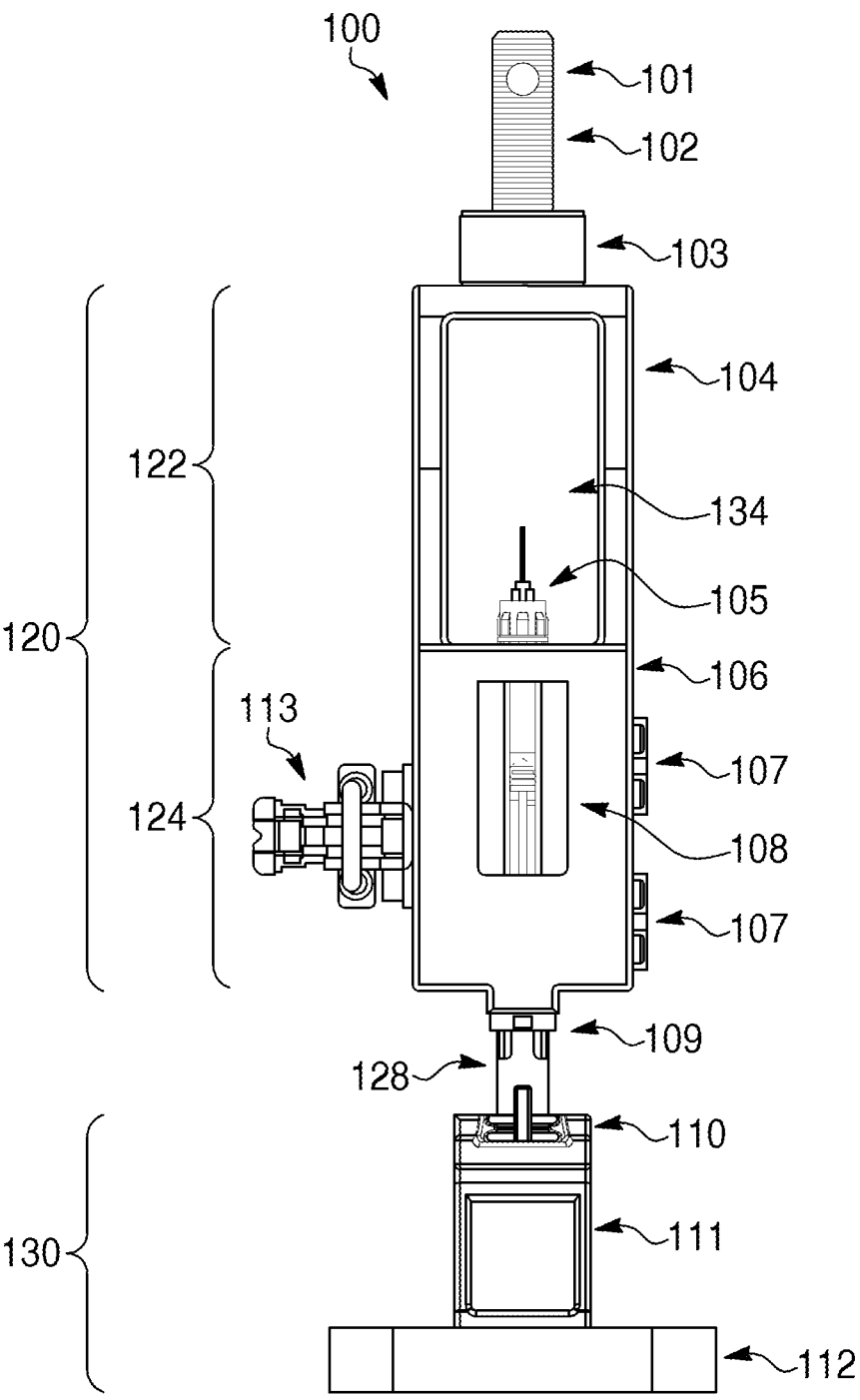
Figure 1C:
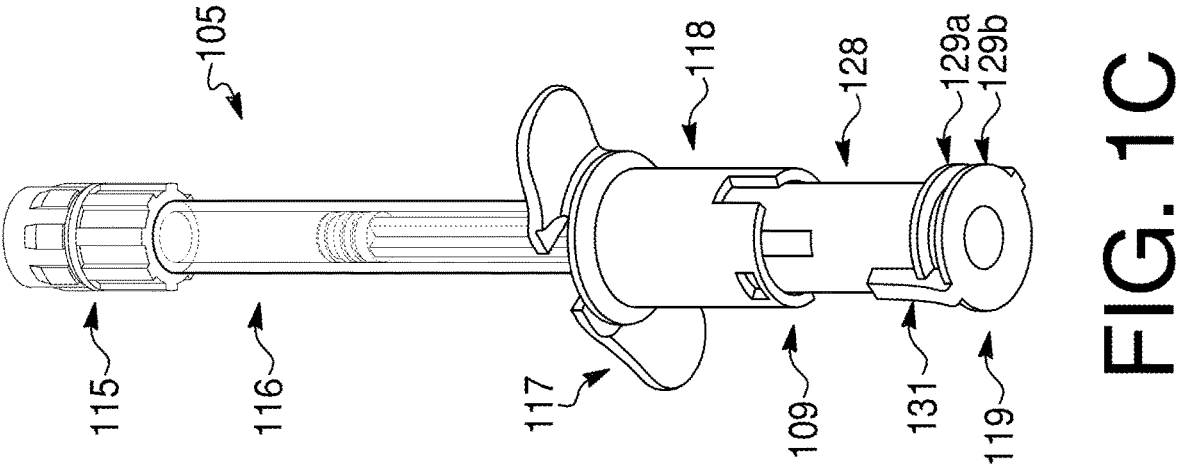
Figure 1B:
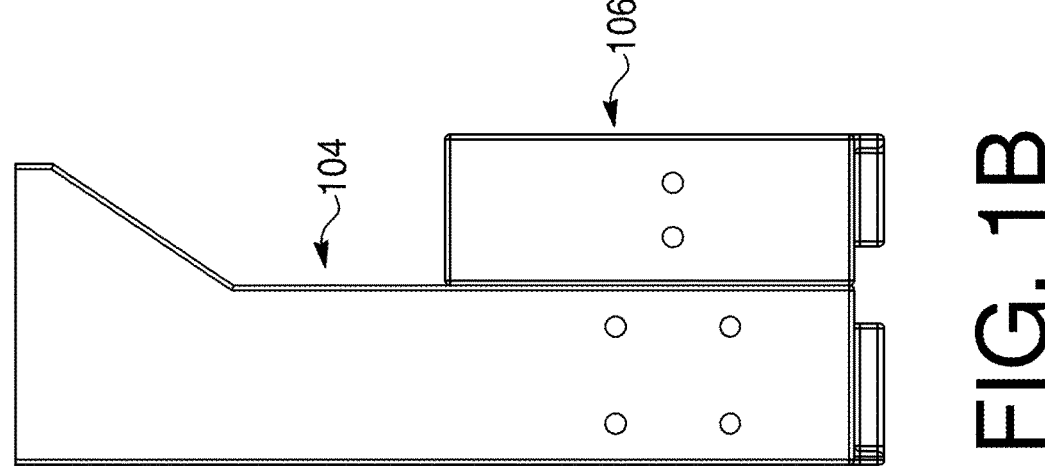

FIG. 1A is a front view of the syringe fixture, FIG. 1B is a side view of the main housing of the syringe fixture, and FIG. 1C is an exemplary syringe that may be utilized with the syringe fixture, according to embodiments of the present disclosure.

Figure 2:
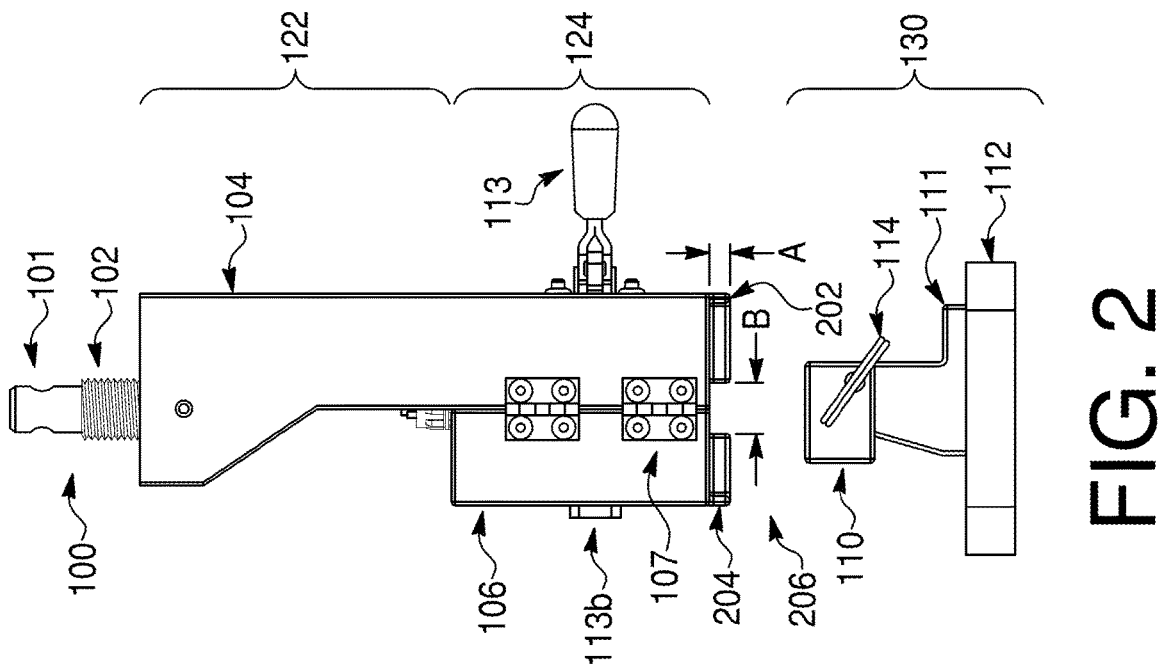

FIG. 2 is a side view of the syringe fixture, according to an embodiment of the present disclosure.

Figure 3:
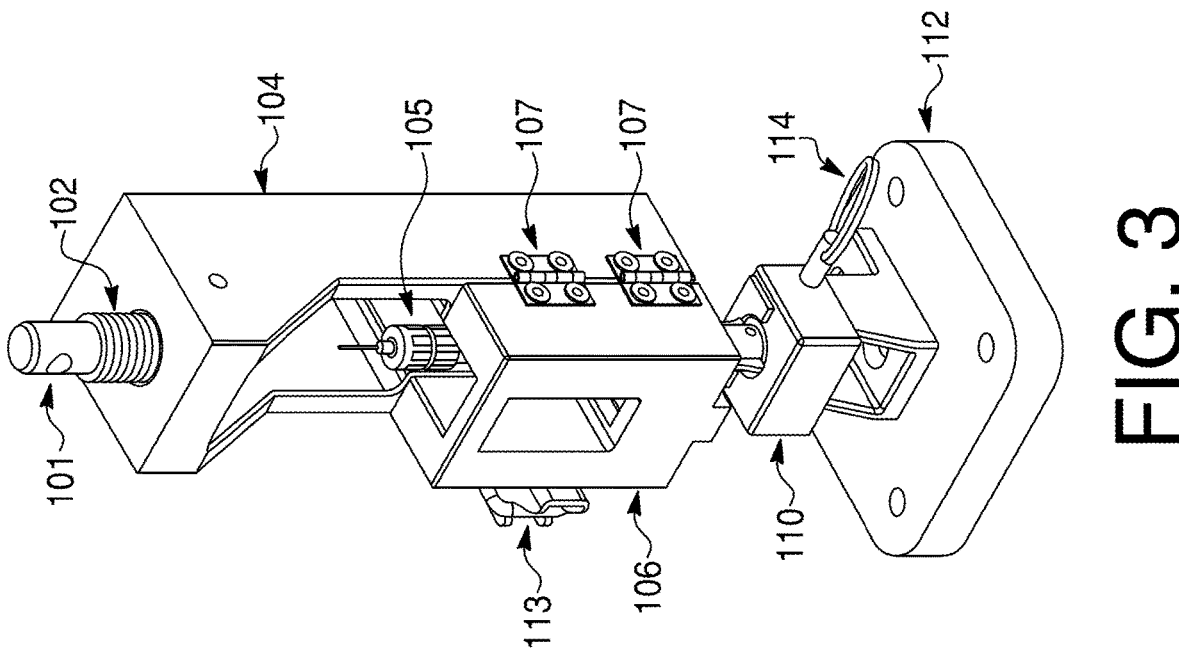

FIG. 3 is a perspective view of the syringe fixture, according to an embodiment of the present disclosure.

Figure 4B:
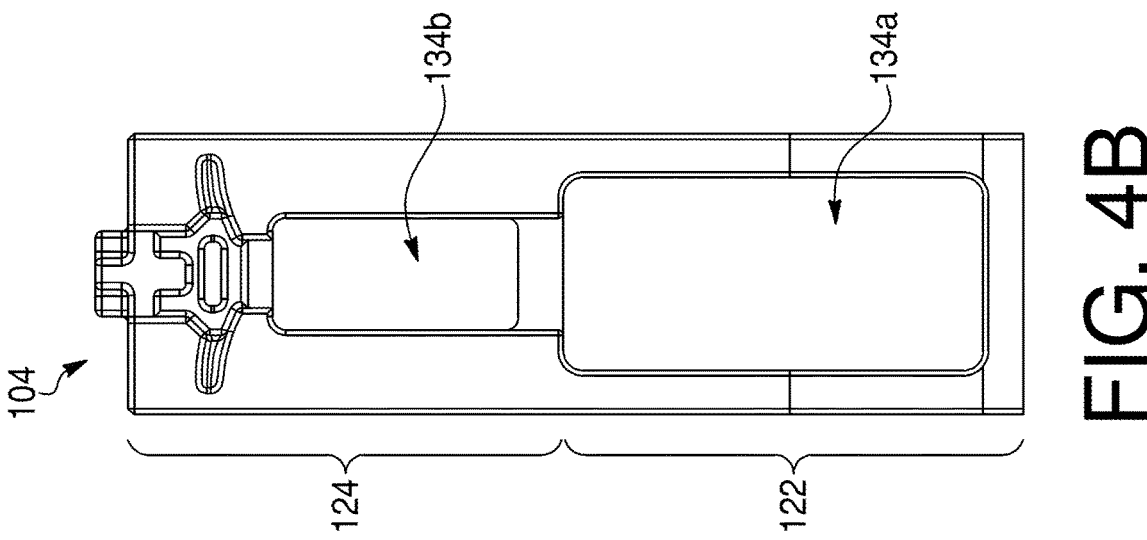
Figure 4A:
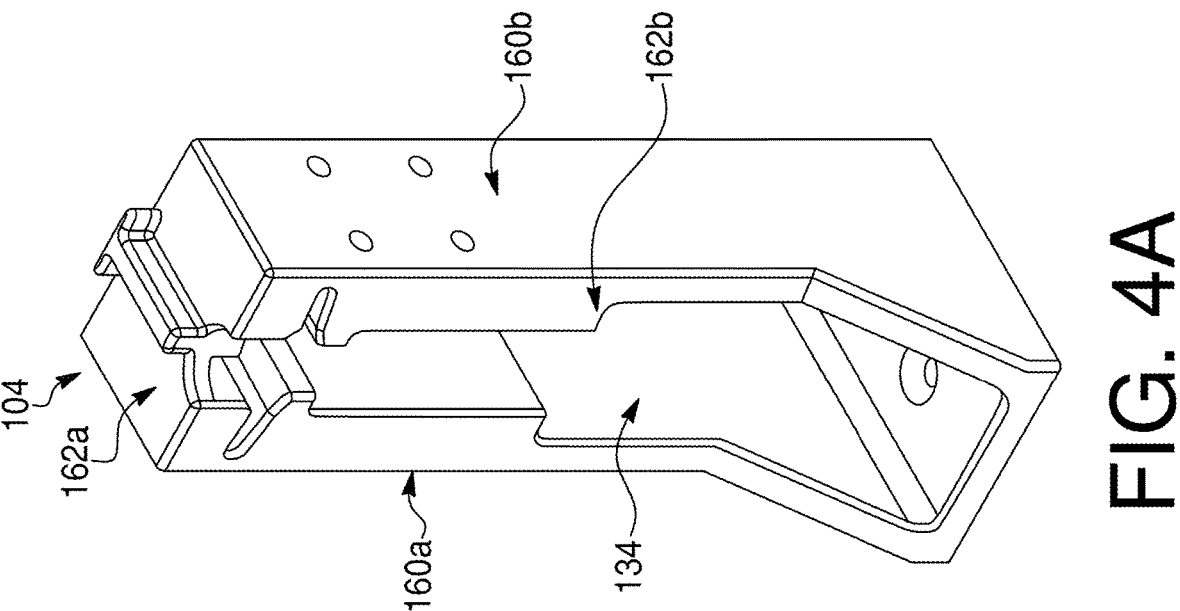
Figure 4D:
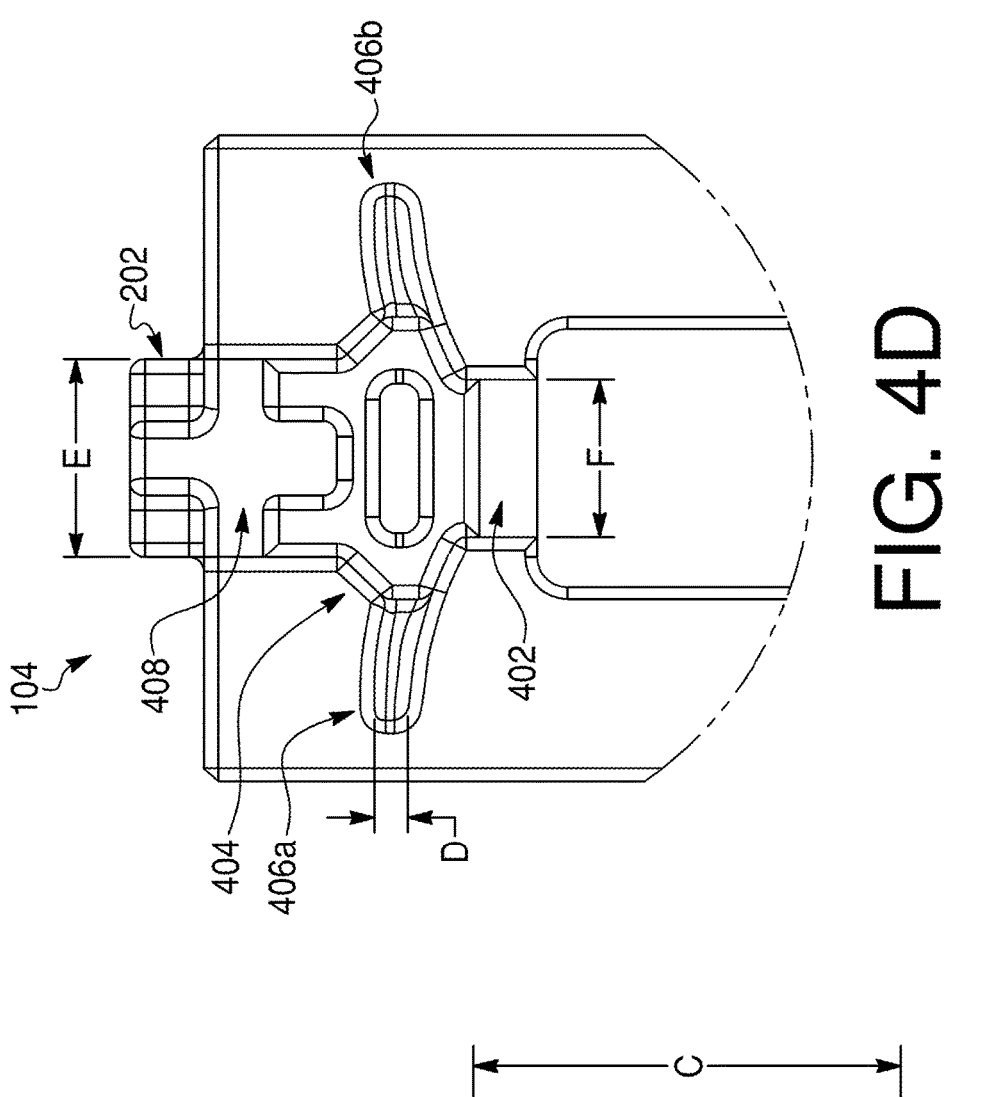
Figure 4C:
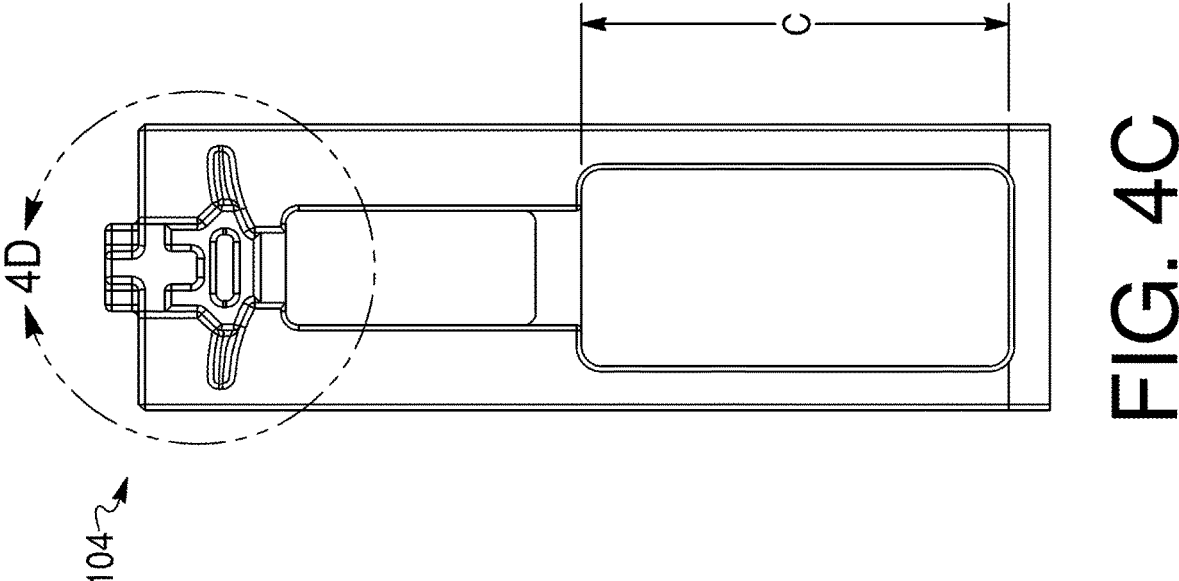

FIG. 4A is a perspective view of the main housing, FIGS. 4B and 4C are front views of the main housing, and FIG. 4D is a detailed view of the second chamber of the main housing, according to embodiments of the present disclosure.

FIGS. 5A-5D are front views of the syringe fixture, including detailed views of the interior of the first chamber, according to embodiments of the present disclosure.

Figures 6A, 6B:
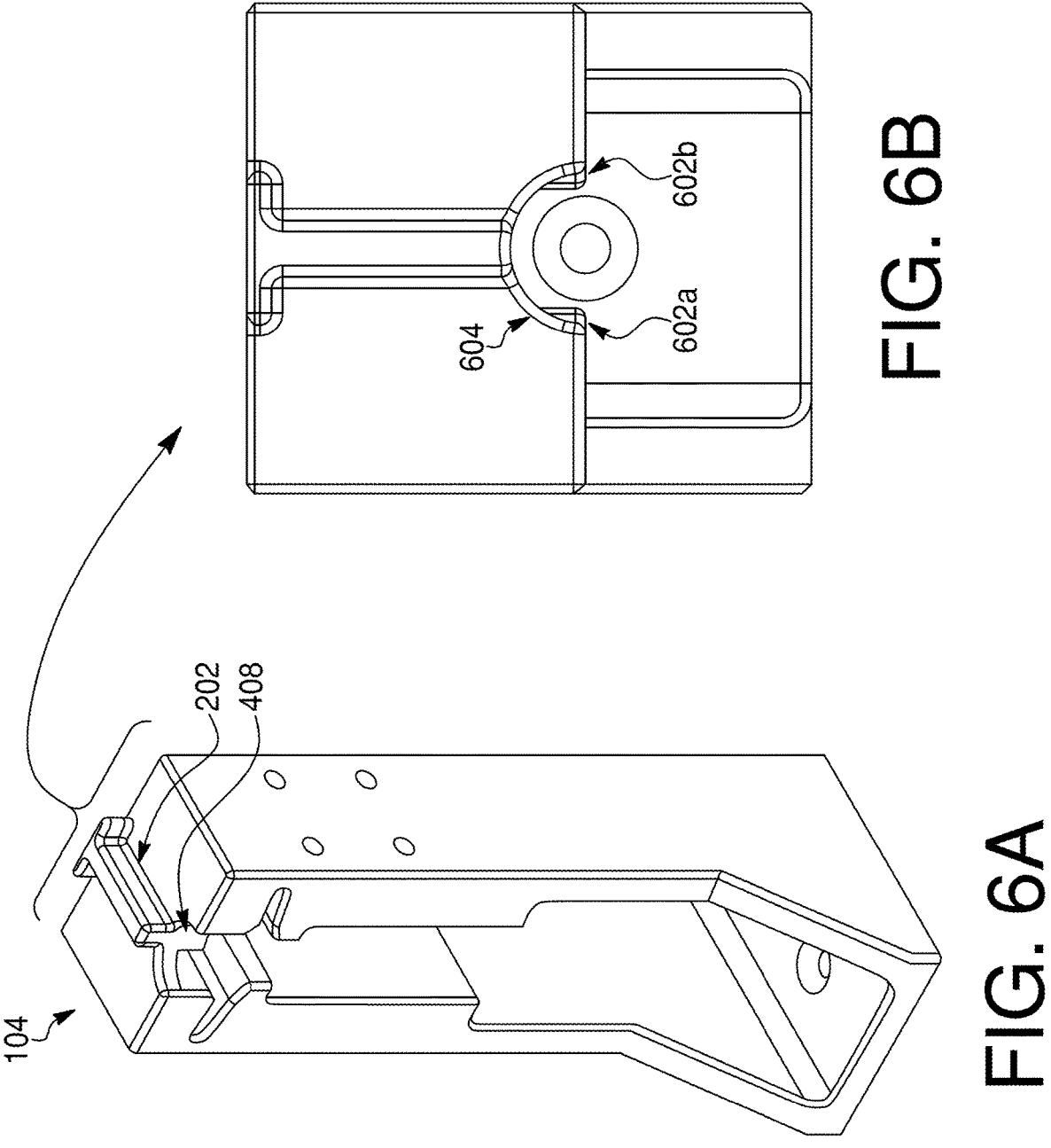
Figure 6D:
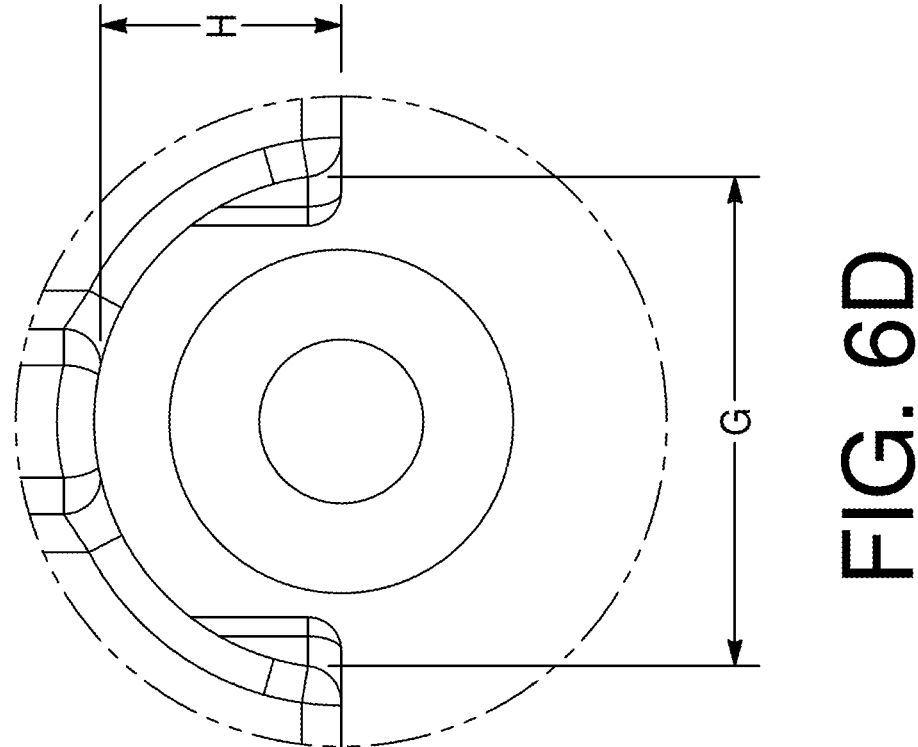
Figure 6C:
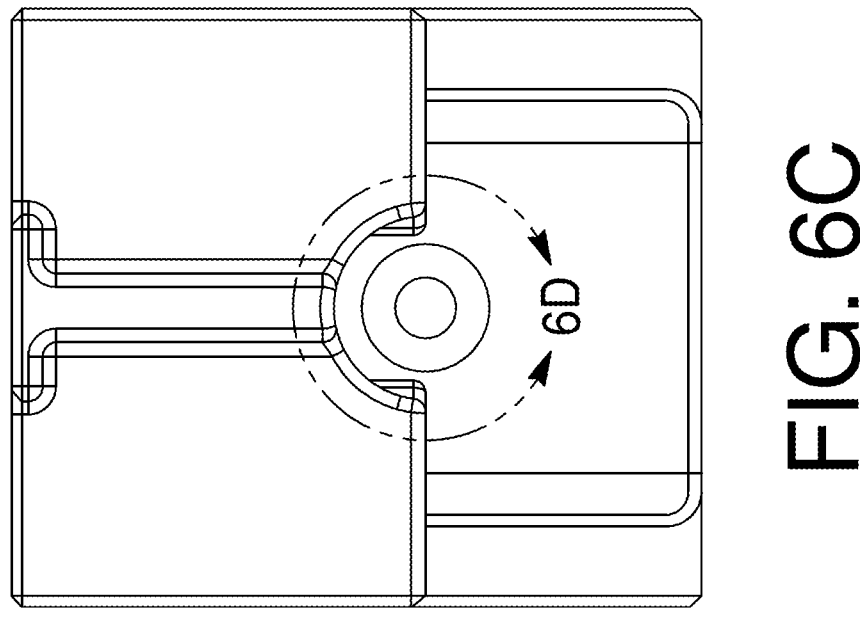

FIG. 6A is a perspective view of the main housing and FIGS. 6B-6D are bottom views of the second chamber, according to embodiments of the present disclosure.

Figures 7A, 7B:
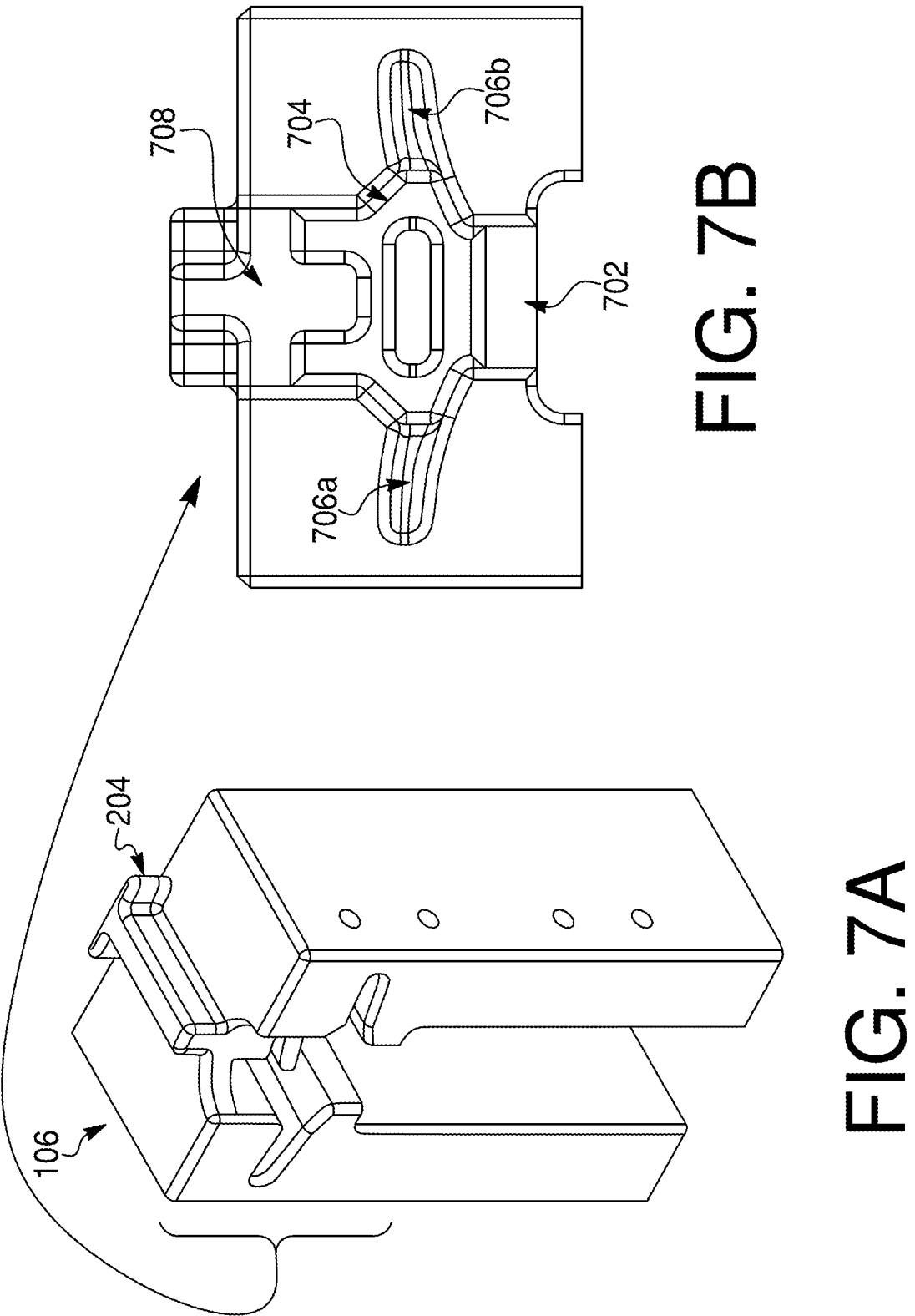
Figure 7D:
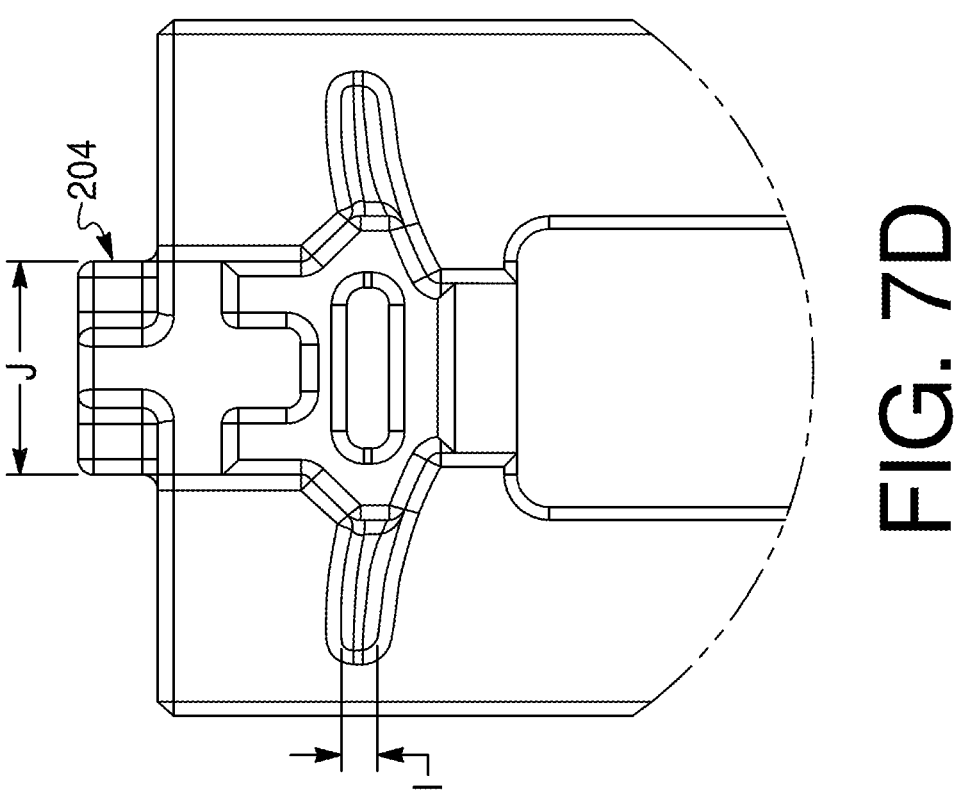
Figure 7C:
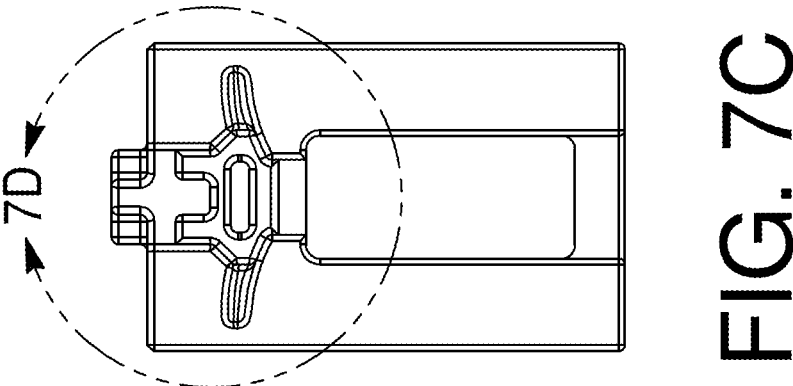

FIG. 7A is a perspective view of the cover for the second chamber and FIGS. 7B-7D are detailed views of the interior of cover, according to embodiments of the present disclosure.

FIG. 8A is a perspective view of the cover for the second chamber and FIGS. 8B and 8C are bottom views of the cover, according to embodiments of the present disclosure.

Figures 9A, 9B:
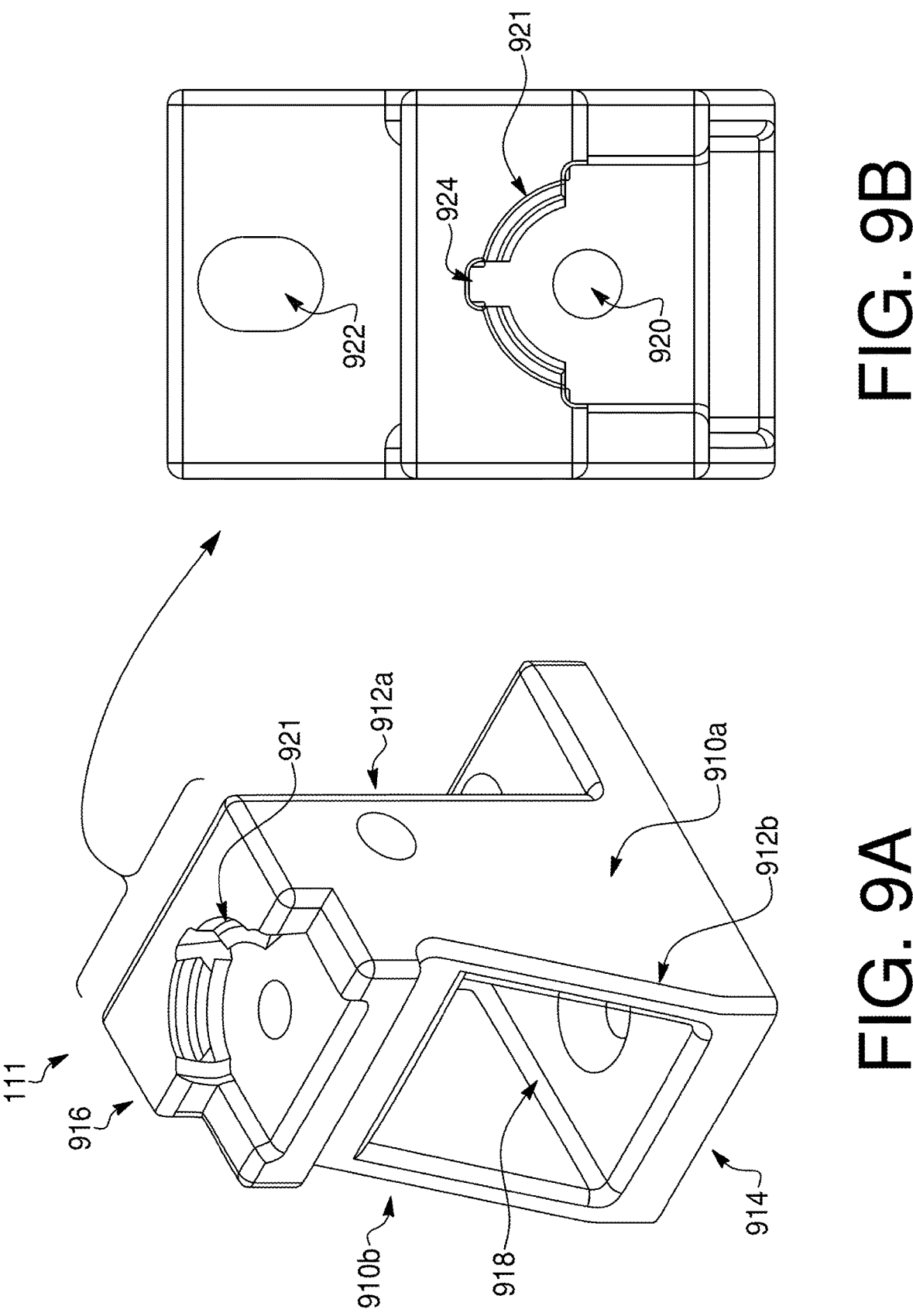
Figure 9D:
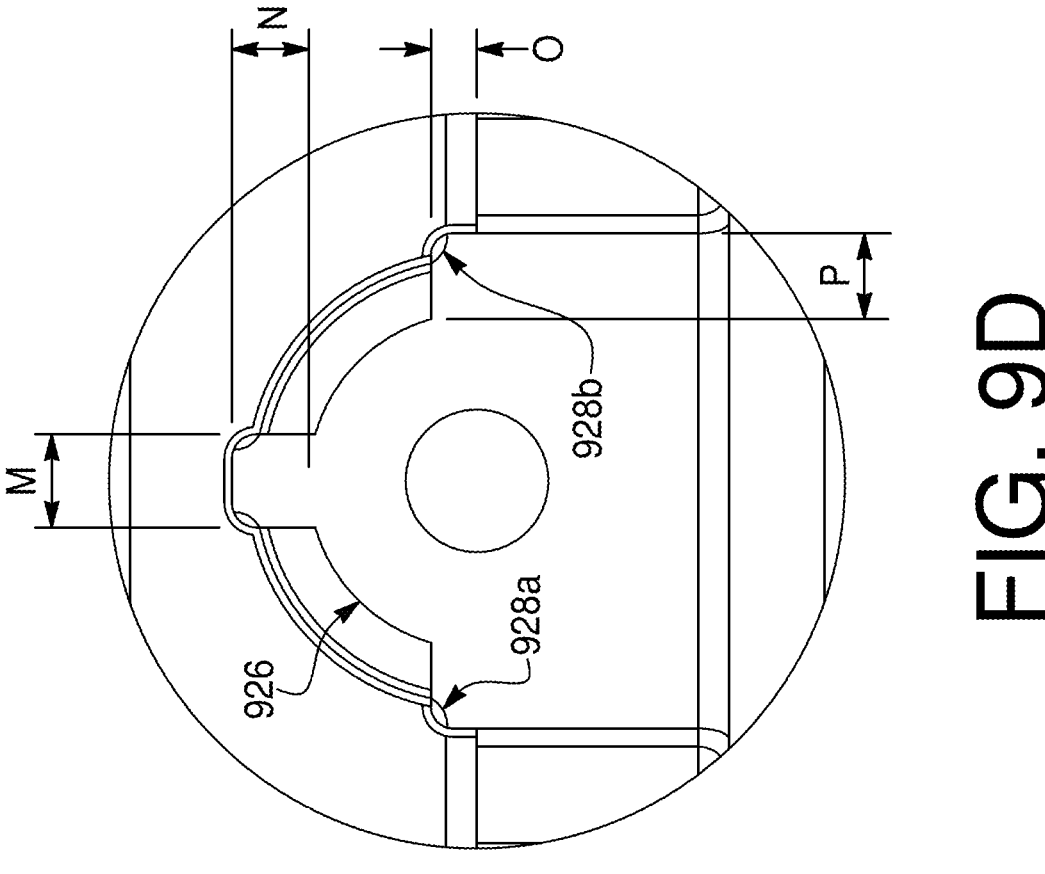
Figure 9C:
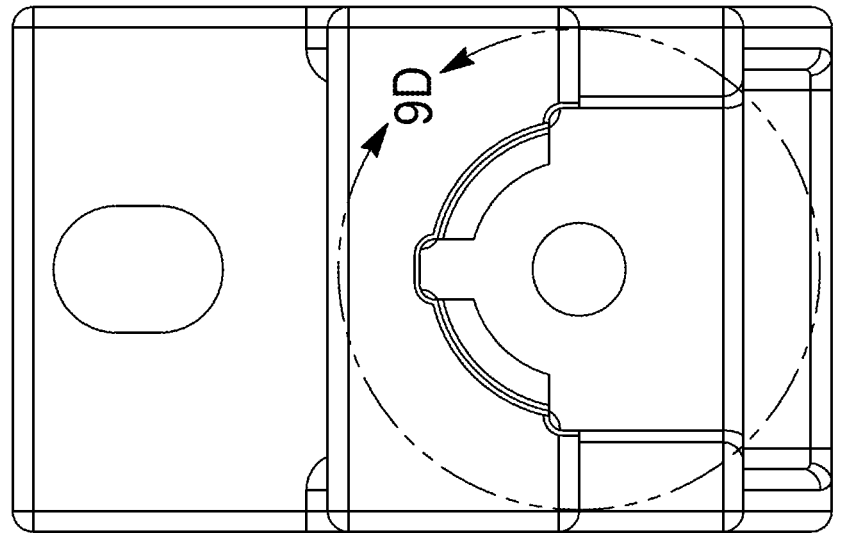

FIG. 9A is a perspective view of the holder of the base portion and FIGS. 9B-9D are top views of the holder, according to embodiments of the present disclosure.

FIGS. 10A-10D are front views of the holder of the base portion, wherein the holder is encasing a syringe, according to embodiments of the present disclosure.

Figure 11A:
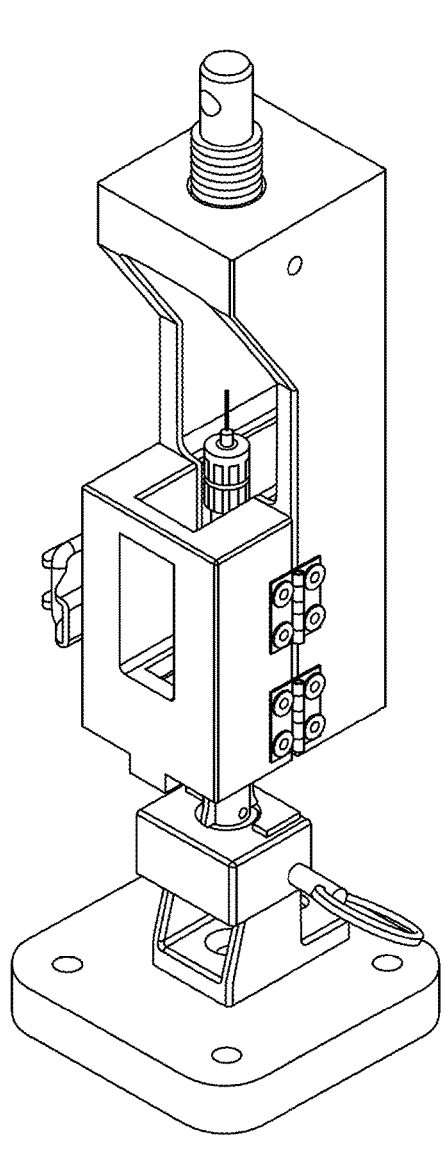
Figure 11B:
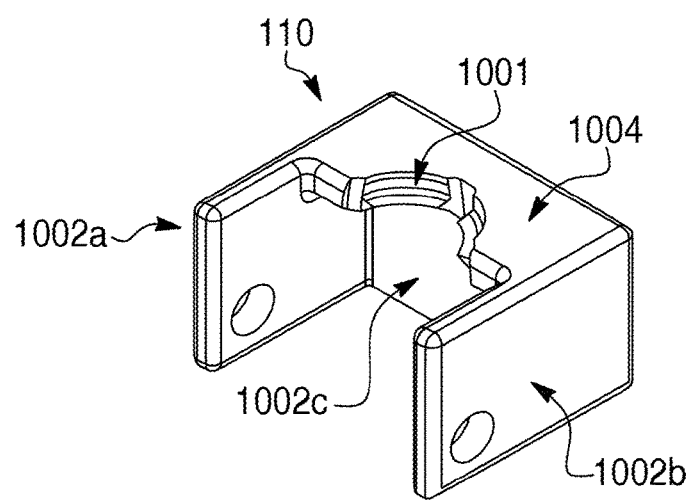
Figure 11C:
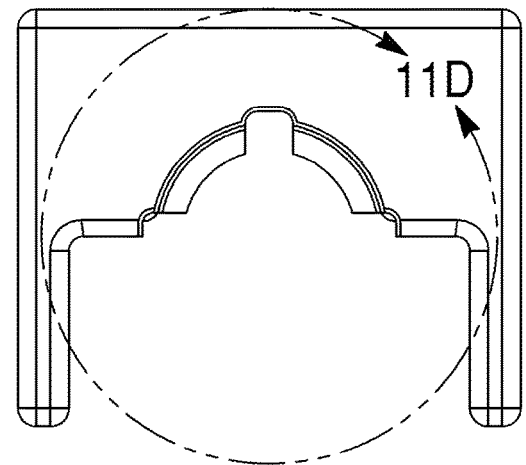
Figure 11D:
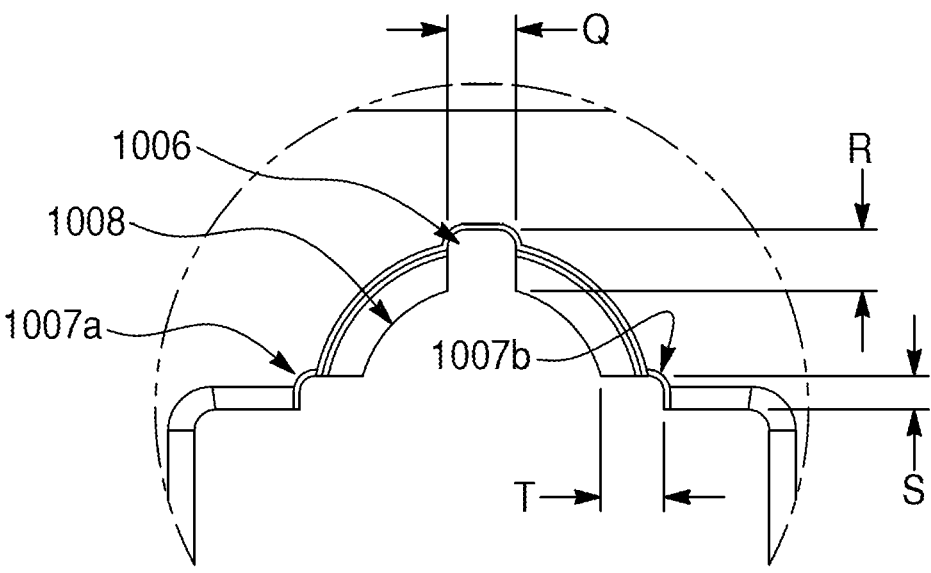
Figure 11E:
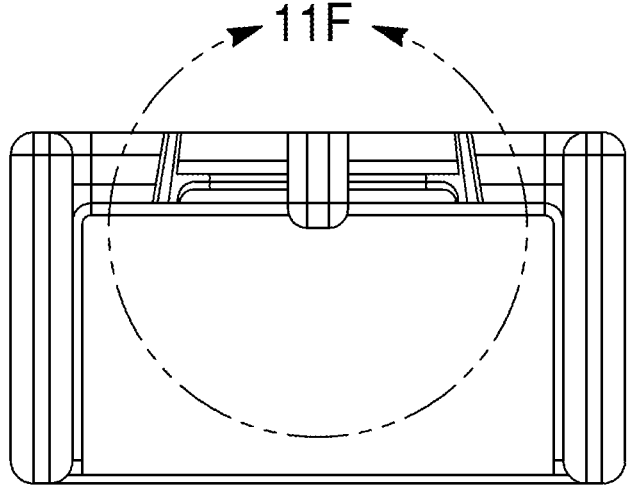
Figure 11F:
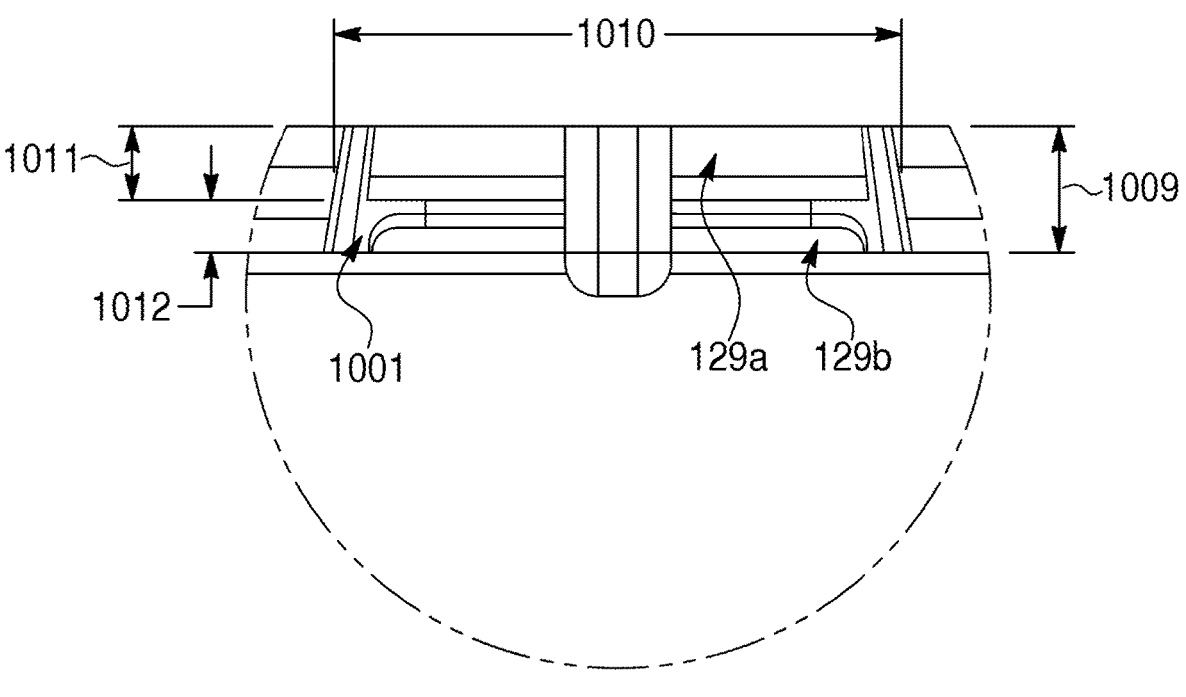

FIG. 11A is a perspective view of the syringe fixture, FIG. 11B is a perspective view of the casing of the base portion of the syringe fixture, FIGS. 11C and 11D are top views of the casing, and FIGS. 11E and 11F are front views of the casing, according to embodiments of the present disclosure.

Figure 12A:
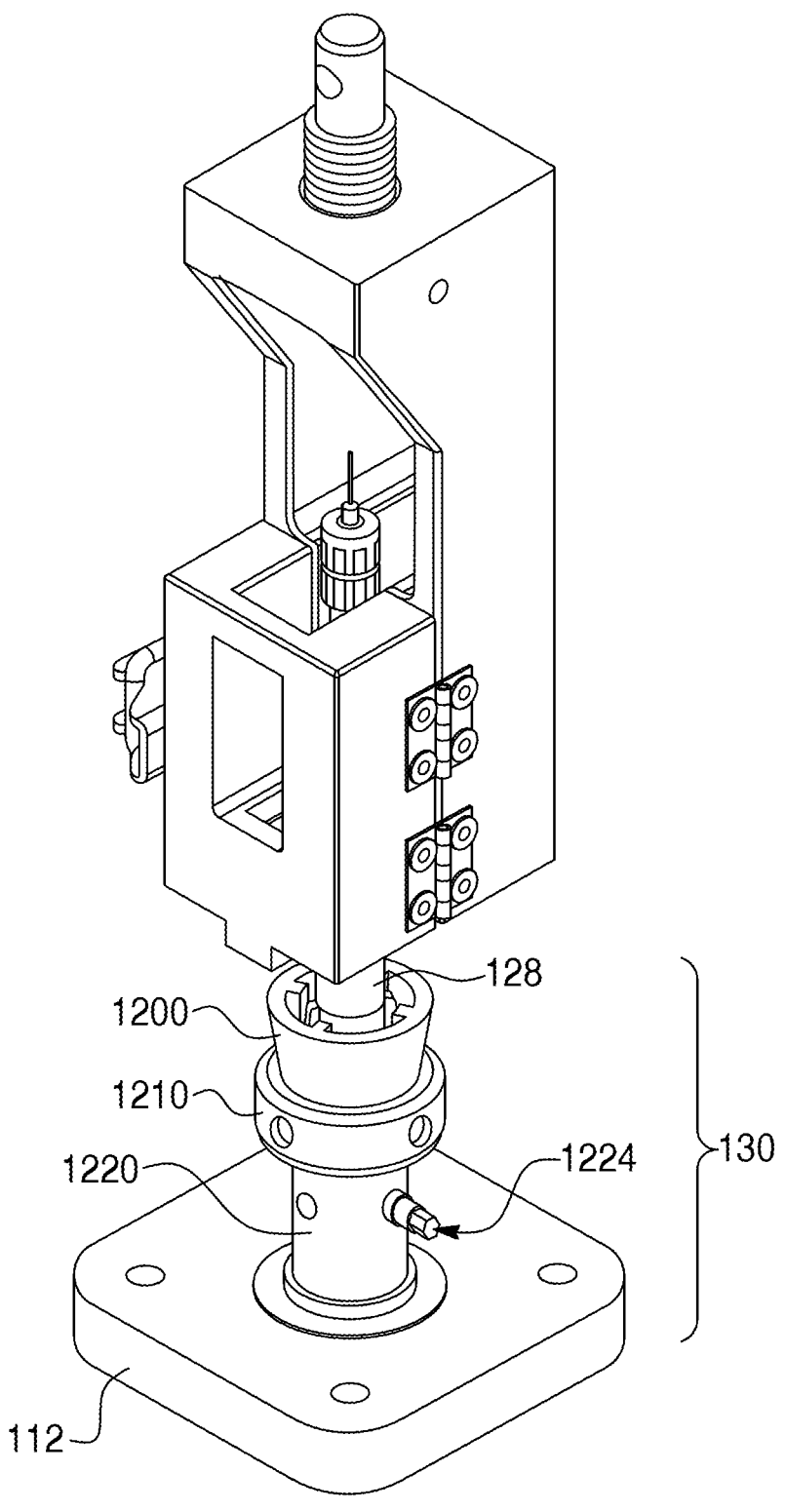
Figures 12B, 12C:
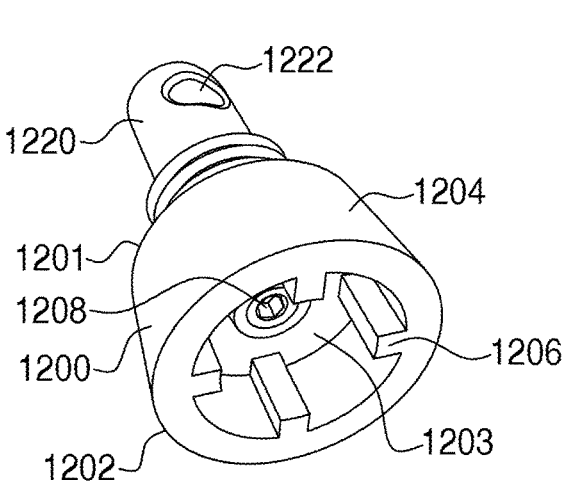
Figures 12D, 12E:
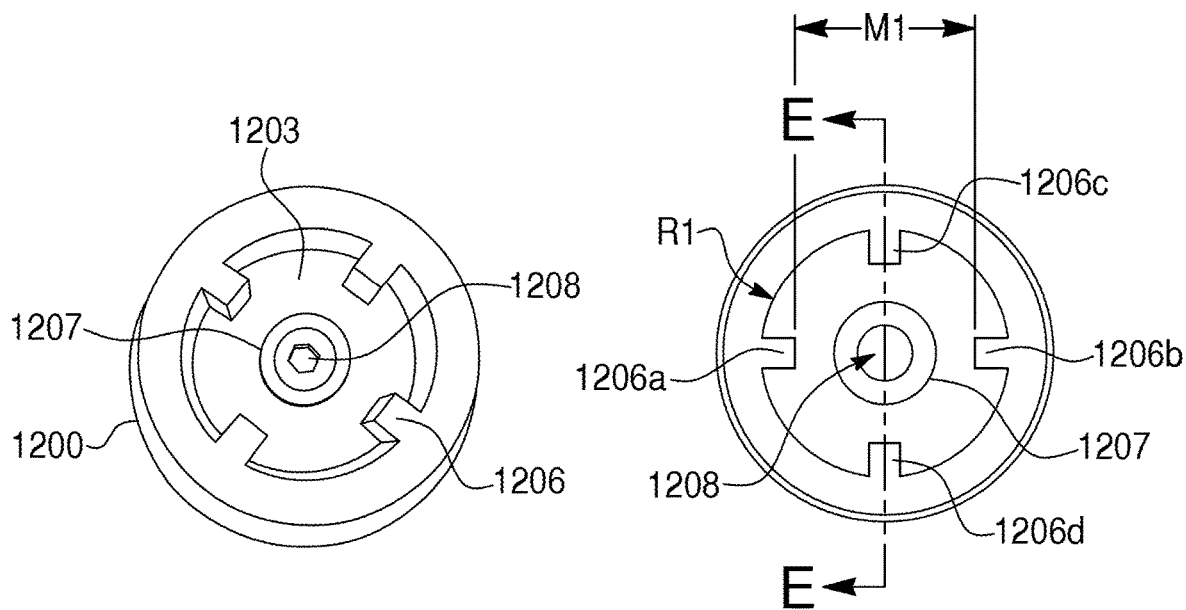

FIG. 12A is a perspective view of the syringe fixture, FIG. 12B is a perspective view of the base portion of the syringe fixture, the base portion including a lug and connector, FIG. 12C is a side view of the base portion, and FIGS. 12D and 12E are top views of the lug, according to embodiments of the present disclosure.

Figure 13A:
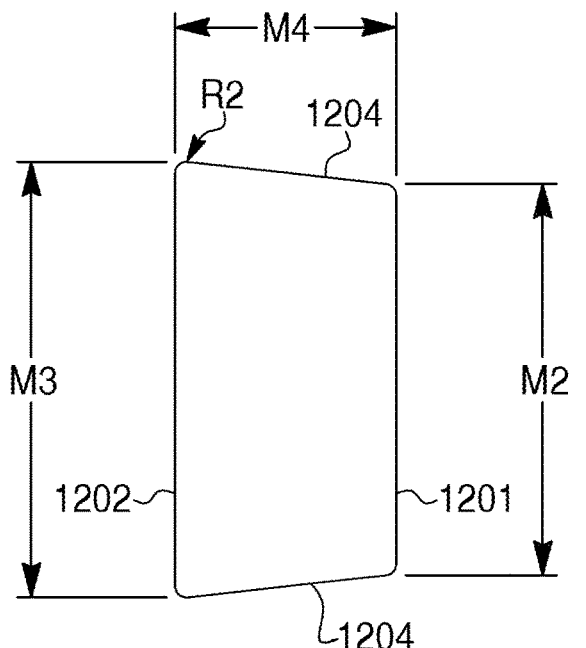
Figure 13B:
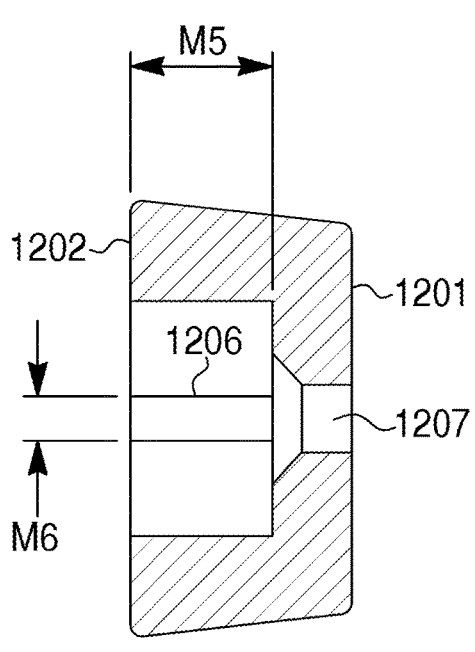

FIG. 13A is a side view of the lug of the base portion in FIG. 12A and FIG. 13B is a cut-out view of the lug according to line E-E of FIG. 12E.

Figure 14:
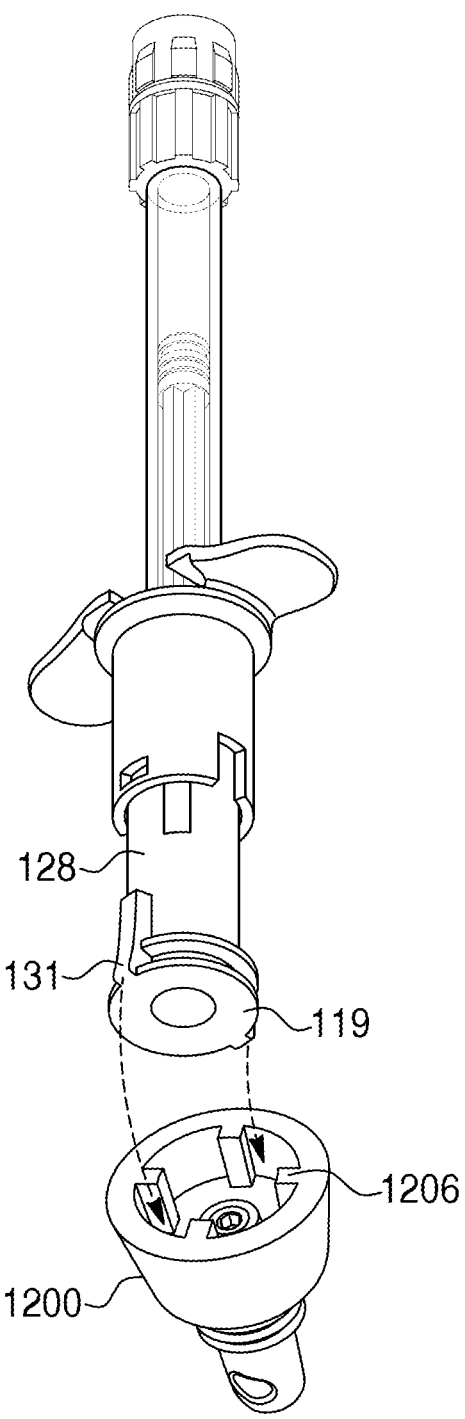

FIG. 14 is an isometric view of how the syringe fits into the base portion, according to embodiments of the disclosure.

Figure 15:
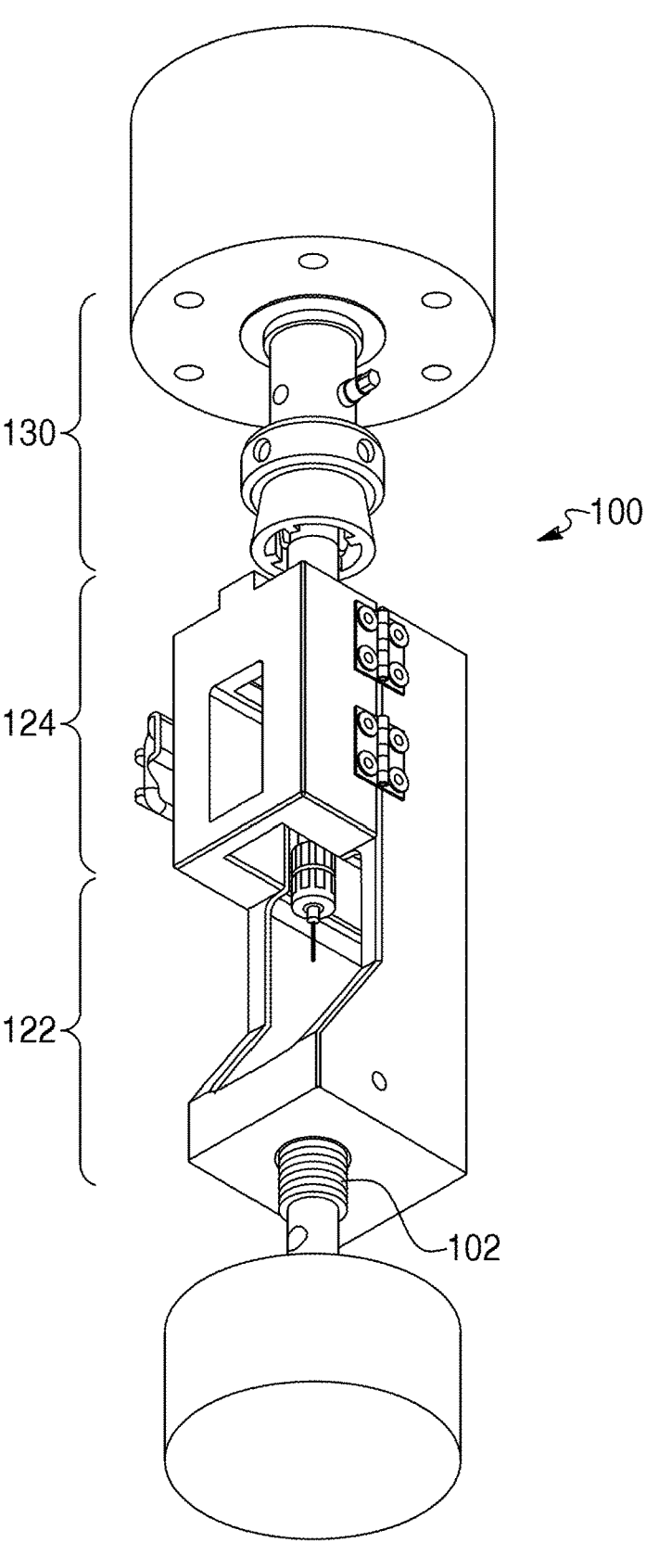

FIG. 15 is a view of the syringe fixture, in an inverted position, according to embodiments of the present disclosure.

Figures 16, 17:
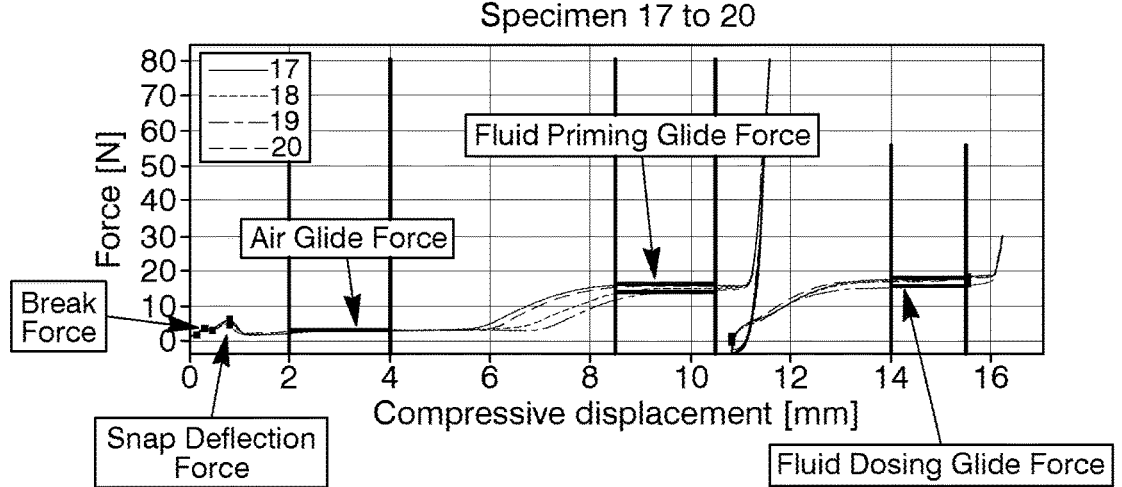

FIG. 16 is a graph depicting injection force profiles for specimens during syringe actuation, according to embodiments of the present disclosure.

FIG. 17 is a table that summarizes mean and standard deviation values for forces of samples, according to embodiments of the present disclosure.

Figure 18:
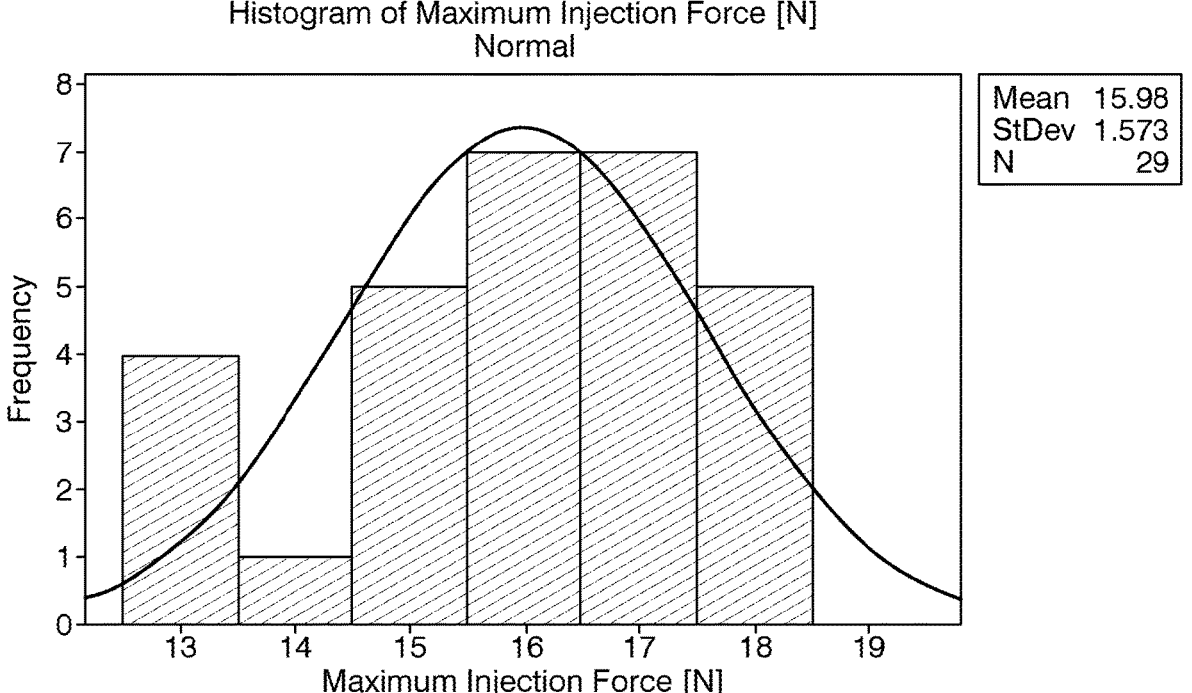

FIG. 18 is a histogram that graphically represents the distribution of maximum injection force for the samples, according to embodiments of the present disclosure.

Figures 19, 20:
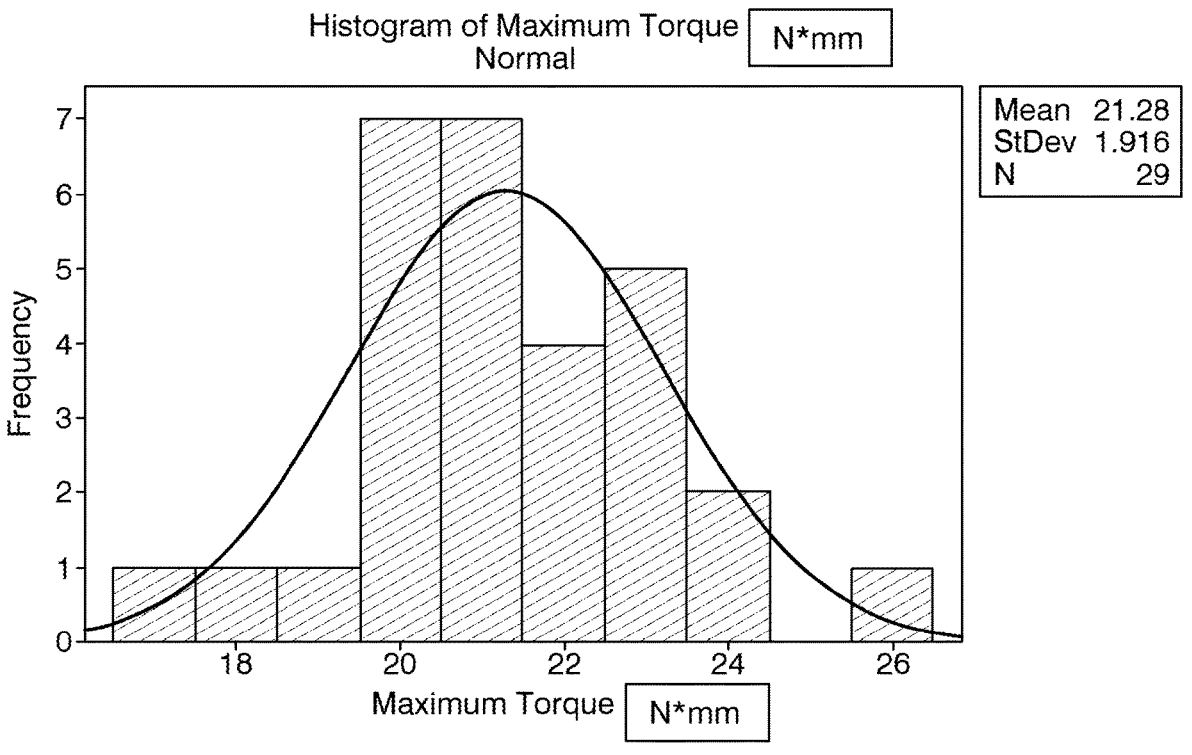

FIG. 19 is a histogram that graphically represents the distribution of maximum torque values measured during the 90-degree rotation of the plunger rod, according to embodiments of the present disclosure.

FIG. 20 is a table that summarizes the torque testing results for syringes with polypropylene flanges, according to embodiments of the present disclosure.

Figure 21:
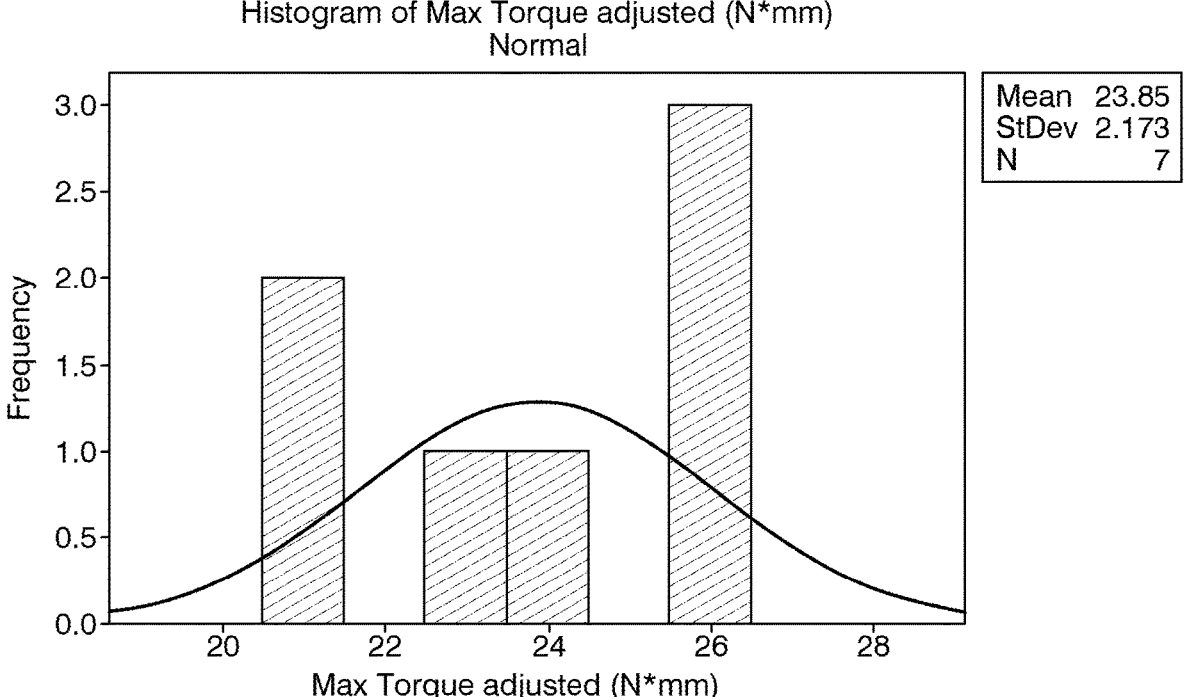

FIG. 21 is a histogram that graphically represents the distribution of maximum torque values for syringes with polypropylene flanges, according to embodiments of the present disclosure.

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." In addition, the terms "first," "second," and the like, herein do not denote any order, quantity, or importance, but rather are used to distinguish an element or a structure from another. Moreover, the terms "a" and "an" herein do not denote a limitation of quantity, but rather denote the presence of one or more of the referenced items.

Notably, for simplicity and clarity of illustration, certain aspects of the figures depict the general structure and/or manner of construction of the various embodiments. Descriptions and details of well-known features and techniques may be omitted to avoid unnecessarily obscuring other features. Elements in the figures are not necessarily drawn to scale; the dimensions of some features may be exaggerated relative to other elements to improve understanding of the example embodiments. For example, one of ordinary skill in the art appreciates that the side views are not drawn to scale and should not be viewed as representing proportional relationships between different components. The side views are provided to help illustrate the various components of the depicted assembly, and to show their relative positioning to one another.

DETAILED DESCRIPTION

Reference will now be made in detail to examples of the present disclosure, which are illustrated in the accompanying drawings. Wherever possible, the same reference numbers will be used throughout the drawings to refer to the same or like parts. In the discussion that follows, relative terms such as "about," "substantially," "approximately," etc. are used to indicate a possible variation of a numerical range in a stated numeric value, as will be designated below.

As disclosed on the Instron® website, www.instron.com/en-us/products/testing-systems/universal-testing-systems, the Instron® systems are large mechanical testing instruments that may be used to perform various mechanical tests, e.g., tensile, compression, bend, peel, and tear. Syringes are an example of a category of devices that may be analyzed using test systems such as the Instron®. As described above and as disclosed on the website for the Instron® systems, existing mechanical test systems may require additional and specific components, in addition to the large and expensive test system themselves, to securely hold devices for testing and analyses. For example, syringes may have varying dimensions, configurations, and/or components, such that a fixture for holding a first type of syringe in the test system, may not be able to hold a second type of syringe in the same test system. Additionally, generic fixtures sold by the test system manufacturers may not properly and securely hold a syringe that is to be tested. During functional force testing, e.g., break loose and/or glide force testing, the plunger rod of the syringe may be pushed to mimic the dosing and injection steps. For a test of torque force, the plunger rod may be twisted to mimic the priming step. If the syringe is not properly secured in the test system, pushing and twisting the syringe may cause the syringe to move around in the test system. Additionally, the forces put on the syringe components, e.g., the plunger rod, may cause the syringe to slip out of the fixture used for the test system if the fixture does not properly secure the syringe in the test system. As mentioned above, during some mechanical tests, e.g., to analyze torque force, syringe components may be twisted to initiate the injection stage. If the syringe is not coaxially aligned with the fixture, additional torque from any misalignment of the syringe with the test system may be induced. Accordingly, it is important that the components of the syringe, syringe fixture, and test system, are coaxially aligned. Any of the above situations, e.g., misalignments or instability in the device being tested by the system, may lead to the testing system providing incorrect measurements and/or require the user to perform multiple tests, which will hamper efficiency.

Although the present disclosure references the Instron® testing mechanism, those of ordinary skill in the art will readily recognize that the concepts of the present disclosure may be utilized with any suitable or comparable testing mechanism or machine (e.g., ZWICKROELL, ADMET, MECMESIN, TEST RESOURCES, etc.). Moreover, although the present disclosure makes reference to testing forces applied to a syringe, those of ordinary skill in the art will readily recognize that reference to a syringe is only exemplary, and that the concepts of the present disclosure may be used in conjunction with any suitable drug delivery device, including, but not limited to, auto-injectors and syringes (both plastic and glass).

Accordingly, the present disclosure is directed to various embodiments of a syringe fixture that holds a syringe with adequate stability and in proper alignment with the test system throughout the entire testing duration. In some examples, the syringe is a precision dose delivery system described in WO 2019/118588 and WO 2020/247686 and US Design application Ser. Nos. 29/760,798 and 29/760,796, which are herein incorporated by reference in their entireties.

Embodiments of the present disclosure relate to a syringe fixture, and, in particular, a syringe fixture for holding a syringe in a test system (e.g., mechanical test systems, such as, e.g., an Instron® test device). FIG. 1A shows a front view of a syringe fixture 100 for a test system. Syringe fixture 100 may be designed to hold any commercially known syringe (or other suitable drug delivery device). Syringe fixture 100 may be formed of any suitable material with sufficient weight and components to aid in the stability of the test fixture, and/or with any characteristics suitable for use in a laboratory setting. For example, syringe fixture 100 may be made from a plastic material and/or other chemically resistant materials. In some embodiments, syringe fixture 100 may be made of metal machined to a desired configuration.

Syringe fixture 100 may include a main housing 120 and base portion 130. Main housing 120 may include a first chamber 122, a second chamber 124, and an opening 134 extending from first chamber 122 to second chamber 124.

First chamber 122 may include a first plurality of walls 150a, 150b, and a second plurality of walls 152a, 152b (FIGS. 5A-5D). First plurality of walls 150a, 150b and second plurality of walls 152a, 152b may define a top opening portion 134a (FIG. 4B). First chamber 122 and top opening portion 134a may be of any suitable size and/or shape so as to contain a portion of syringe 105, as will be discussed in detail below. In some variations, top opening portion 134a may not be opened, but may be a solid wall connected to walls 150a, 150b, 152a, and 152b to provide additional structure and support to the testing fixture.

Figures 5A, 5B:
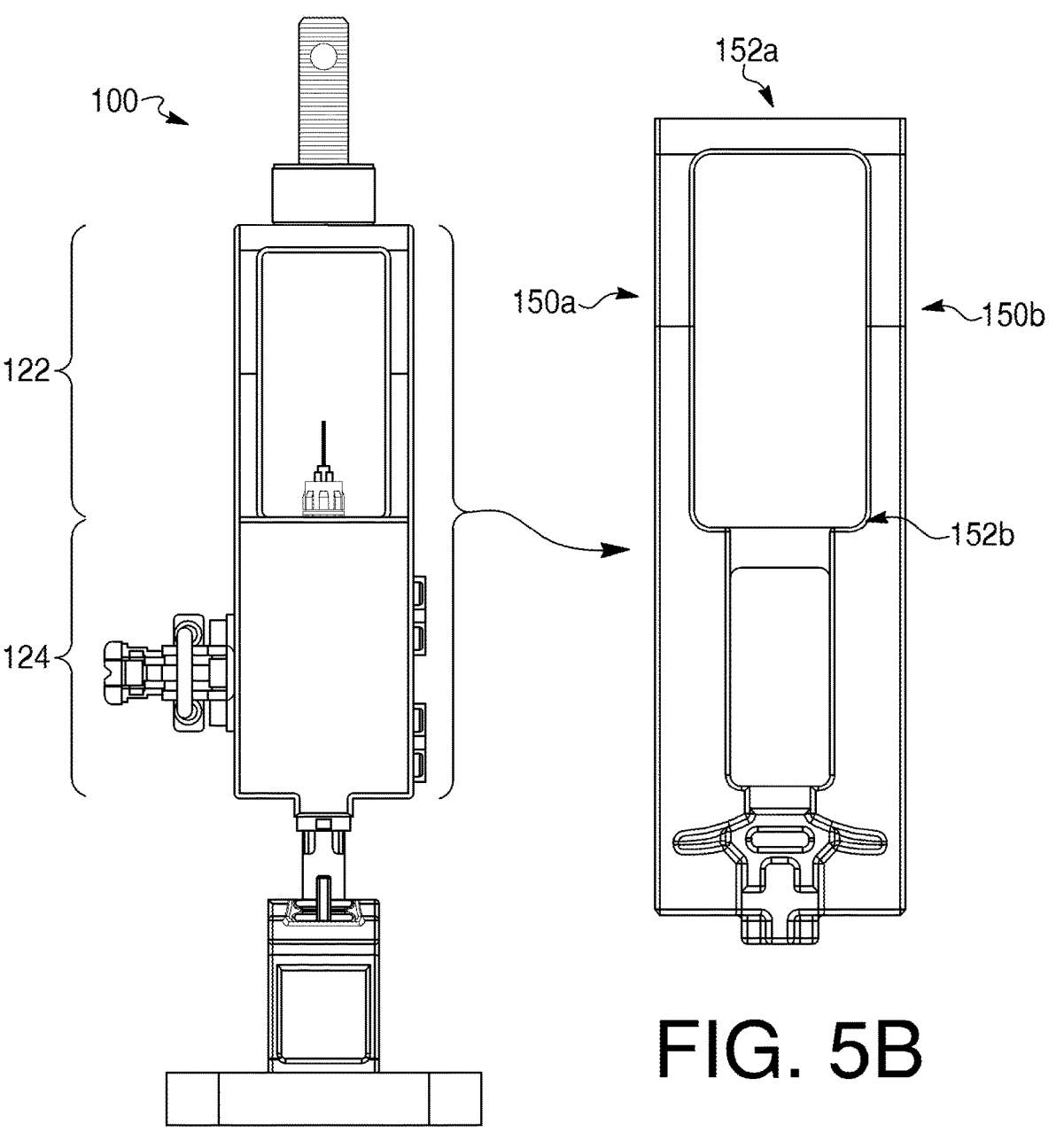
Figures 5C, 5D:
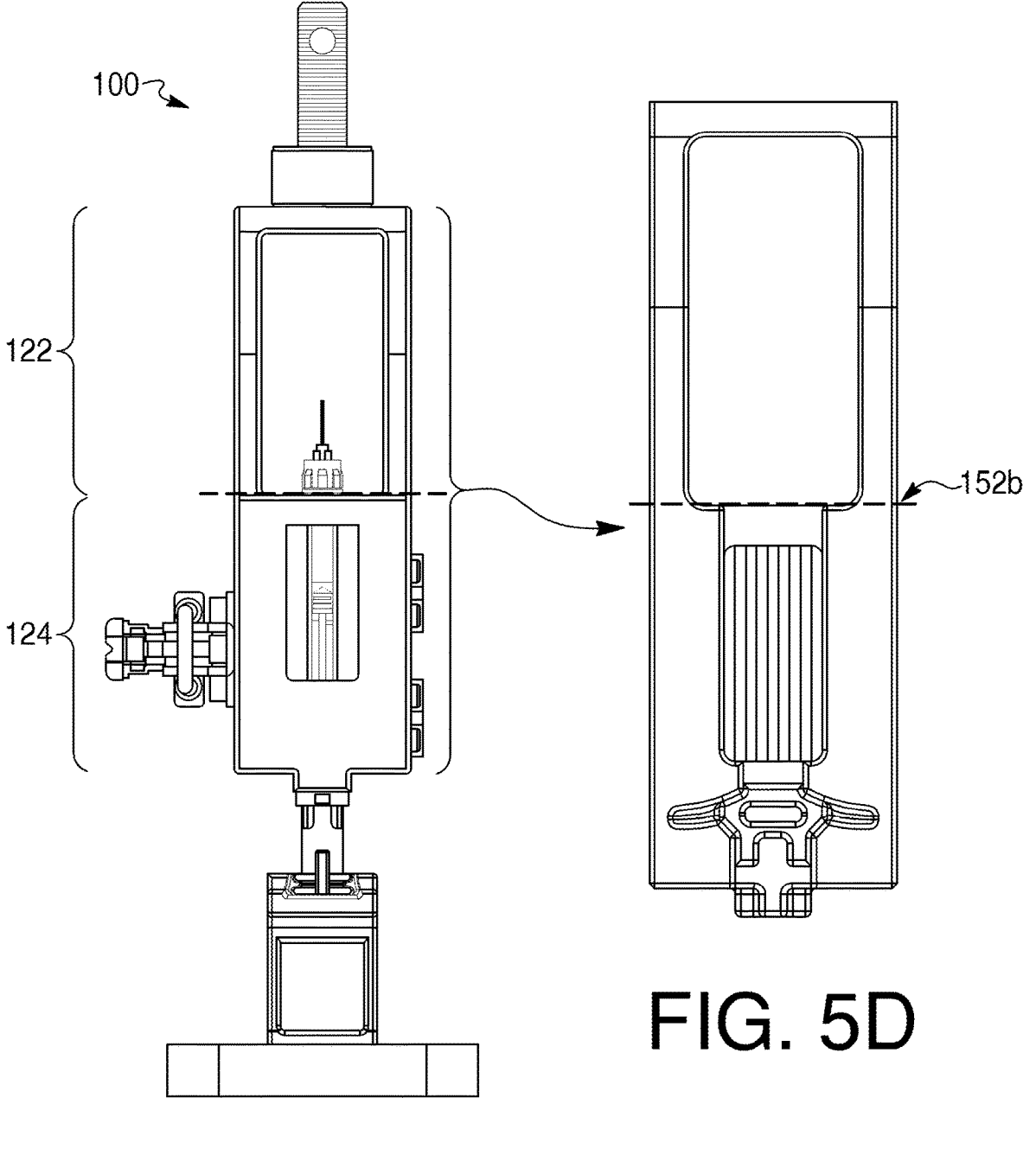

Second chamber 124 may include a first plurality of walls 160a, 160b and a second plurality of walls 162a, 162b (FIG. 4A). First plurality of walls 160a, 160b and second plurality of walls 162a, 162b may define a bottom opening portion 134b (FIG. 4B). In some variations, bottom opening portion 134b may not be opened, but may be a solid wall connected to walls 160a, 160b, 162a, and 162b to provide additional structure and support to the testing fixture. Second chamber 124 may also include a cover 106. Cover 106 may be attached to second chamber 124 via any suitable attachment means. For example, cover 106 may be attached to second chamber 124 via a hinge 107. In some embodiments, cover 106 may be attached to second chamber 124 via a pair of hinges 107. Cover 106 may be solid (FIG. 5A) or cover 106 may include a window 108 allowing user to see into the interior of second chamber 124 and/or the body of syringe 105 and the syringe contents (FIG. 5C). Window 108 may be an opening or may be made from a translucent material. Cover 106 may be moved and/or secured via any appropriate closure 113, e.g., a handle or knob, to allow the user to properly insert syringe 105 into second chamber 124. Cover 106 may contain a receiving feature 113b for the closure 113 to secure to cover 106. For example, cover 106 may be opened and closed using closure 113. Closure 113 may also be used to lock cover 106 onto second chamber 124 by attaching to receiving feature 113b to securely hold syringe 105. Referring to FIG. 1A, and relative to cover 106, the portion of syringe fixture 100 including first chamber 122 and second chamber 124 may be referred to as a case 104.

Referring to FIG. 2, second chamber 124 may include a chamber extension 202 extending from a bottom section of second chamber 124. Cover 106 may include a cover extension 204 extending from a bottom section of cover 106. Chamber extension 202 is also shown in FIG. 6A and cover extension 204 is also shown in FIG. 7A. Chamber extension 202 and cover extension 204 may provide additional stability to second chamber 124 and main housing 120. In other examples, chamber extension 202 and cover extension 204 may provide a view of plunger 128, also referred to herein as plunger rod 128, as it approaches flange body 118. A height of the extensions may be chosen so as to not interfere with components of syringe 105, e.g., syringe plunger end 109. Each of the extensions, represented as A in FIG. 2, may have a height ranging from about 4.00 mm to about 6.00 mm. For example, a height of each extension may range from about 4.20 mm to about 5.80 mm, about 4.40 mm to about 5.60 mm, about 4.60 mm to about 5.40 mm, about 4.80 mm to about 5.20 mm, about 4.90 mm to about 5.10 mm, or about 5.00 mm. In some examples, each extension may have a height ranging from about 4.80 mm to about 5.20 mm or about 5.00 mm+0.20 mm. As shown in FIG. 1A, when syringe 105 is inserted into second chamber 124, a portion of syringe 105, e.g., plunger end 109 and plunger 128 may extend between and past chamber extension 202 and cover extension 204. Referring to FIG. 2, a clearance 206 between chamber extension 202 and cover extension 204 may be configured to allow sufficient space for plunger end 109 and plunger 128 and so that main housing 120 may comfortably fit on top of base portion 130. Clearance 206 has a width, represented as B in FIG. 2, ranging from about 12.00 mm to about 14.00 mm, about 12.35 mm to about 13.95, about 12.55 mm to about 13.75 mm, about 12.75 mm to about 13.55 mm, about 12.95 mm to about 13.35 mm, about 13.05 mm to about 13.25 mm, or about 13.15 mm. In some examples, clearance 206 has a width ranging from 12.95 mm to about 13.35 mm or about 13.15 mm±0.20 mm.

Second chamber 124 may be of any suitable size and/or shape so as to contain a portion of syringe 105. For example, flange 117 and flange body 118 may fit into second chamber 124 such that syringe 105 is stable and secured. Referring to FIGS. 4B-4D, second chamber 124 may include various cavities configured to securely hold flange 117 and flange body 118 such that there is limited space or no space between flange 117 and the cavities of second chamber 124.

Second chamber 124 may include a first cavity 402, second cavity 404, and third cavity 408. First cavity 402 may be of any suitable size and/or shape so as to contain a portion of the syringe body 116 distal from flange 117. As shown in FIG. 4D, first cavity 402 may have a diameter, represented as F, ranging from about 9.00 mm to about 12.00 mm, 10.00 mm to about 11.00 mm, about 10.10 mm to about 10.90 mm, about 10.20 mm to about 10.80 mm, about 10.30 mm to about 10.80 mm, about 10.40 mm to about 10.80 mm, about 10.50 mm to about 10.70 mm, or about 10.60 mm. In some examples, first cavity 402 has a diameter ranging from 9.60 mm to about 10.40 mm or about 10.80 mm+0.20 mm.

Second cavity 404 may be of any suitable size and/or shape so as to contain flange 117. Second cavity 404 may include arm cavities 406a, 406b. Arm cavities 406a, 406b may have a height, represented as D in FIG. 4D, ranging from about 2.00 mm to about 2.50 mm, about 2.05 mm to about 2.45 mm, about 2.10 mm to about 2.40 mm, about 2.15 mm to about 2.40 mm, about 2.20 mm to about 2.40 mm or about 2.30 mm. In some examples, arm cavities 406a, 406b has a height ranging from about 2.22 mm to about 2.38 mm or about 2.30 mm+0.08 mm.

Third cavity 408 may be of any suitable size and/or shape so as to contain flange body 118. As shown in FIG. 4D, third cavity 408 may include an extension 202 extending past the bottom portion of second chamber 124 and as described in detail above. Third cavity 408 and extension 202 may have a diameter, represented as E in FIG. 4D, ranging from about 13.00 mm to about 14.00 mm, about 13.10 mm to about 13.90 mm, about 13.15 mm to about 13.80 mm, about 13.20 mm to about 13.70 mm, about 13.22 mm to about 13.62 mm, about 13.32 mm to 13.52 mm, or about 13.42 mm. In some examples, the diameter ranges from about 13.22 mm to about 13.62 mm or 13.42±0.20 mm.

Referring to FIGS. 6A-6D, third cavity 408 may be of any suitable size and/or shape so as to contain flange body 118. In the bottom view of second chamber 124 (FIG. 6B), third cavity 408 may include a rim 604 and shoulder portions 602a, 602b. As shown in FIG. 6D, a distance between an inner curve of shoulder portion 602a and an inner curve of shoulder portion 602b, represented as G, may range from about 13.00 mm to about 14.00 mm, about 13.05 mm to about 13.90 mm, about 13.10 mm to about 13.80 mm, about 13.15 mm to about 13.70 mm, about 13.20 mm to about 13.65 mm, about 13.22 mm to about 13.62 mm, about 13.32 mm to 13.52 mm, or about 13.42 mm. In some examples, the distance between the inner curve of shoulder portion 602a and the inner curve of shoulder portion 602b ranges from about 13.22 mm to about 13.62 mm or 13.42±0.20 mm.

In some examples, a distance from an inner curve of rim 604 to a bottom portion of either shoulder portion 602a, 602b, represented as H in FIG. 6D, may range from about 6.00 mm to about 7.50 mm, about 6.10 mm to about 7.40 mm, about 6.20 mm to about 7.30 mm, about 6.30 mm to about 7.20 mm, about 6.40 mm to about 7.10 mm, about 6.50 mm to about 7.00 mm, about 6.52 mm to about 6.92 mm, about 6.62 mm to about 6.82 mm, or about 6.72 mm. In some examples, the distance from the inner curve of rim 604 to a bottom portion of either shoulder portion 602a, 602b ranges from about 6.52 mm to about 6.92 mm or about 6.72±0.20 mm.

Cover 106, which may be attached to second chamber 124 to enclose and securely hold portions of syringe 105, e.g., flange 117 and flange body 118, may be of any suitable size and/or shape. For example, once flange 117 and flange body 118 are inserted into second chamber 124, cover 106 may be placed over second chamber 124 to enclose such portions of syringe 105. Referring to FIGS. 7A-7D, cover 106 may include various cavities corresponding to cavities 402, 404, 408 of second chamber 124. The cavities of cover 106 may be configured to securely hold flange 117 and flange body 118 such that there is limited space or no space between flange 117 and the corresponding cavity walls of the covering 106. For example, a portion of syringe 105 and cover 106 may have a fit such that there is limited space or no space between a portion of syringe 105 and the interior of cover 106.

Cover 106 may include a first cavity 702, second cavity 704, and third cavity 708. First cavity 702 may be of any suitable size and/or shape so as to contain a portion of the syringe body 116 distal to flange 117. As shown in FIG. 7D, first cavity 702 may have a diameter ranging from about 10.00 mm to about 11.00 mm, about 10.10 mm to about 10.90 mm, about 10.20 mm to about 10.80 mm, about 10.30 mm to about 10.80 mm, about 10.40 mm to about 10.80 mm, about 10.50 mm to about 10.70 mm, or about 10.60 mm. In some examples, first cavity 702 has a diameter ranging from 9.60 mm to about 10.40 mm or about 10.80 mm±0.20 mm.

Second cavity 704 may be of any suitable size and/or shape so as to contain flange 117. Second cavity 704 may include arm cavities 706a, 706b. Arm cavities 706a, 706b may have a height, represented as I in FIG. 7D, ranging from about 2.00 mm to about 2.50 mm, about 2.05 mm to about 2.45 mm, about 2.10 mm to about 2.40 mm, about 2.15 mm to about 2.40 mm, or about 2.20 mm to about 2.40 mm or about 2.30 mm. In some examples, arm cavities 706a, 706b has a height ranging from about 2.22 mm to about 2.38 mm or about 2.30 mm+0.08 mm.

Third cavity 708 may be of any suitable size and/or shape so as to contain a portion of flange body 118. As shown in FIG. 7D, third cavity 708 may include an extension 204 extending past the bottom portion of cover 106 and as described in detail above. Third cavity 708 and extension 204 may have a diameter, represented as J in FIG. 7D, ranging from about 13.00 mm to about 14.00 mm, about 13.10 mm to about 13.90 mm, about 13.15 mm to about 13.80 mm, about 13.20 mm to about 13.70 mm, about 13.22 mm to about 13.62 mm, about 13.32 mm to 13.52 mm, or about 13.42 mm. In some examples, the diameter ranges from about 13.22 mm to about 13.62 mm or 13.42±0.20 mm.

Referring to FIGS. 8A-8C, third cavity 708 may be of any suitable size and/or shape so as to contain plunger body 118. In the bottom view of cover 106 (FIG. 8B), third cavity 708 may include a rim 804 and shoulder portions 802a, 802b. As shown in FIG. 8C, a distance between an inner curve of shoulder portion 802a and an inner curve of shoulder portion 802b, represented as K, may range from about 13.00 mm to about 14.00 mm, about 13.05 mm to about 13.90 mm, about 13.10 mm to about 13.80 mm, about 13.15 mm to about 13.70 mm, about 13.20 mm to about 13.65 mm, about 13.22 mm to about 13.62 mm, about 13.32 mm to 13.52 mm, or about 13.42 mm. In some examples, the distance between the inner curve of shoulder portion 802a and the inner curve of shoulder portion 802b ranges from about 13.22 mm to about 13.62 mm or 13.42±0.20 mm.

In some examples, a distance from an inner curve of rim 804 to a bottom portion of either shoulder portion 802a, 802b, represented as L in FIG. 8C, may range from about 6.00 mm to about 7.50 mm, about 6.10 mm to about 7.40 mm, about 6.20 mm to about 7.30 mm, about 6.30 mm to about 7.20 mm, about 6.40 mm to about 7.10 mm, about 6.50 mm to about 7.00 mm, about 6.52 mm to about 6.92 mm, about 6.62 mm to about 6.82 mm, or about 6.72 mm. In some examples, the distance from the inner curve of rim 804 to a bottom portion of either shoulder portion 802a, 802b ranges from about 6.52 mm to about 6.92 mm or about 6.72±0.20 mm.

One of more of the plurality of cavities 402, 404, 408, of second chamber 124 and one or more of the plurality of cavities 702, 704, 708 of cover 106, may include features to aid in the gripping of syringe 105 within the cavities of second chamber 124 and cover 106. For example, one of more of the plurality of cavities may include a polished, silicone, or elastic coating, providing a closer and/or tighter hold between portions of syringe 105 and the cavities of second chamber 124 and cover 106. In other examples, the dimensions of the plurality of cavities can be adjusted to rectangular geometries to aid in the gripping of syringe 105. In yet other examples, support structures, geometric features, or textures, e.g., ribbing, bumps, or protrusions, can be included to aid in the gripping of syringe 105.

In embodiments of the present disclosure, second chamber 124 may be removable from main housing 120, as shown with the dashed line in FIG. 5C. As detailed above, second chamber 124 and plurality of cavities 402, 404, 408 may have various sizes and/or shapes so to as properly receive and securely hold a portion of syringe 105, e.g., flange 117 and flange body 118. It is understood that different syringes may have different sizes and/or configurations. In order to adapt syringe fixture 100 so that various commercially available syringes may be used with syringe fixture 100, it may be helpful to have different configurations of a second chamber 124 that may be interchanged in main housing 120. For example, a second chamber 124 with a first configuration may be removed from main housing 120, in order for a different second chamber with a different configuration to be inserted into main housing 120. In some embodiments, syringe fixture 100 may be sold or provided in a kit along with a plurality of second chambers, wherein each second chamber has a different configuration to be used with a different syringe.

Base portion 130 may include a casing 110, holder 111, and support 112. Holder 111 may be configured to securely hold a plunger top 119 of syringe 105. Referring to FIGS. 1C, 2, 3, and 9A-9D, plunger top 119 may be inserted into holder 111. Holder 111 may have any appropriate configuration to hold plunger top 119 in a stable position between a first ring 129a and a second ring 129b and in coaxial alignment with the rest of syringe fixture 100. For example, holder 111 may have a first plurality of sidewalls 910a, 910b and a second plurality of sidewalls 912a, 912b, wherein the plurality of sidewalls extend between a bottom portion 914 and a top portion 916, forming a cavity 918. In some examples, bottom portion 914 may have a length greater than a length of top portion 916, as shown in FIG. 9A. The plurality of sidewalls may have various configurations to provide a stable support for syringe 105. For example, one or more of the second plurality of sidewalls 912a, 912b may slant or curve inward towards cavity 918.

Plunger top 119 of syringe 105 may fit into top portion 916 of holder 111 (see FIGS. 9A-9D). Top portion 916 may include a holding portion 921 configured to receive plunger top 119 in between first ring 129a and second ring 129b. Top portion 916 may also include a notch 924. A portion of plunger top 119, e.g., a protrusion 131, may fit into notch 924 to securely hold plunger top 119. Top portion 916 may also include an opening 920 for holding a portion of syringe 105, e.g., a trigger or injection button. Bottom portion 914 may include an opening 922 configured for receiving a fastener, e.g., a screw, to secure bottom portion 914 to support 112.

FIG. 9D shows various measurements of top portion 916. For example, notch 924 may have a width, represented as M, ranging from about 2.50 mm to about 3.50 mm, about 2.70 mm to about 3.30 mm, about 2.70 mm to about 3.10 mm, about 2.80 mm to about 3.00 mm, or about 2.90 mm. In some examples, the notch 924 has a width ranging from about 2.70 mm to about 3.10 mm or 2.90±0.20 mm. Additional measurements of top portion 916 may be made in reference to an inner circumference 926. Top portion 916 may include a plurality of shoulder portions 928a, 928b, wherein a distance from an outer edge of either shoulder portion 928a, 928b to inner circumference 926, represented as P, ranges from about 2.00 mm to about 3.00 mm, about 2.14 mm to about 2.94 mm, about 2.24 mm to about 2.84 mm, about 2.34 mm to about 2.54 mm, or about 2.44 mm.

In some examples, the distance from an outer edge of either shoulder portion 928a, 928b to inner circumference 926 ranges from about 2.34 mm to about 2.54 mm or 2.44 mm+0.10 mm. A distance from a top edge of either shoulder portion 928a, 928b to a central axis of inner circumference 926, represented as O, ranges from about 1.00 mm to about 2.00 mm, about 1.15 mm to about 1.85 mm, about 1.25 mm to about 1.65 mm, about 1.35 mm to about 1.55 mm, or about 1.45 mm. In some examples, the distance from a top edge of either shoulder portion 928a, 928b to a central axis of inner circumference 926 ranges from about 1.25 mm to about 1.65 mm or 1.45 mm±0.20 mm. A top edge of notch 924 to inner 1 circumference 926 ranges, represented as N, from about 2.00 mm to about 3.00 mm, about 2.20 mm to about 2.80 mm, about 2.30 mm to about 2.60 mm, about 2.37 mm to about 2.57 mm, or about 2.47 mm. In some examples, the distance from top edge of notch 924 to inner circumference 926 ranges from about 2.37 mm to about 2.57 mm or 2.47 mm+0.10 mm.

Plurality of shoulder portions 928a, 928b may be configured to receive a protrusion of plunger top 119. In some embodiments, plunger top 119 may comprise a plurality of protrusions, wherein the protrusions may be received in any combination of notch 924 and shoulder portions 928a, 928b. For example, if the protrusions on plunger top 119 are equidistant from each other (e.g., FIG. 1C), the syringe may be turned and still be able to be received in holder 111.

Figures 10A, 10B:
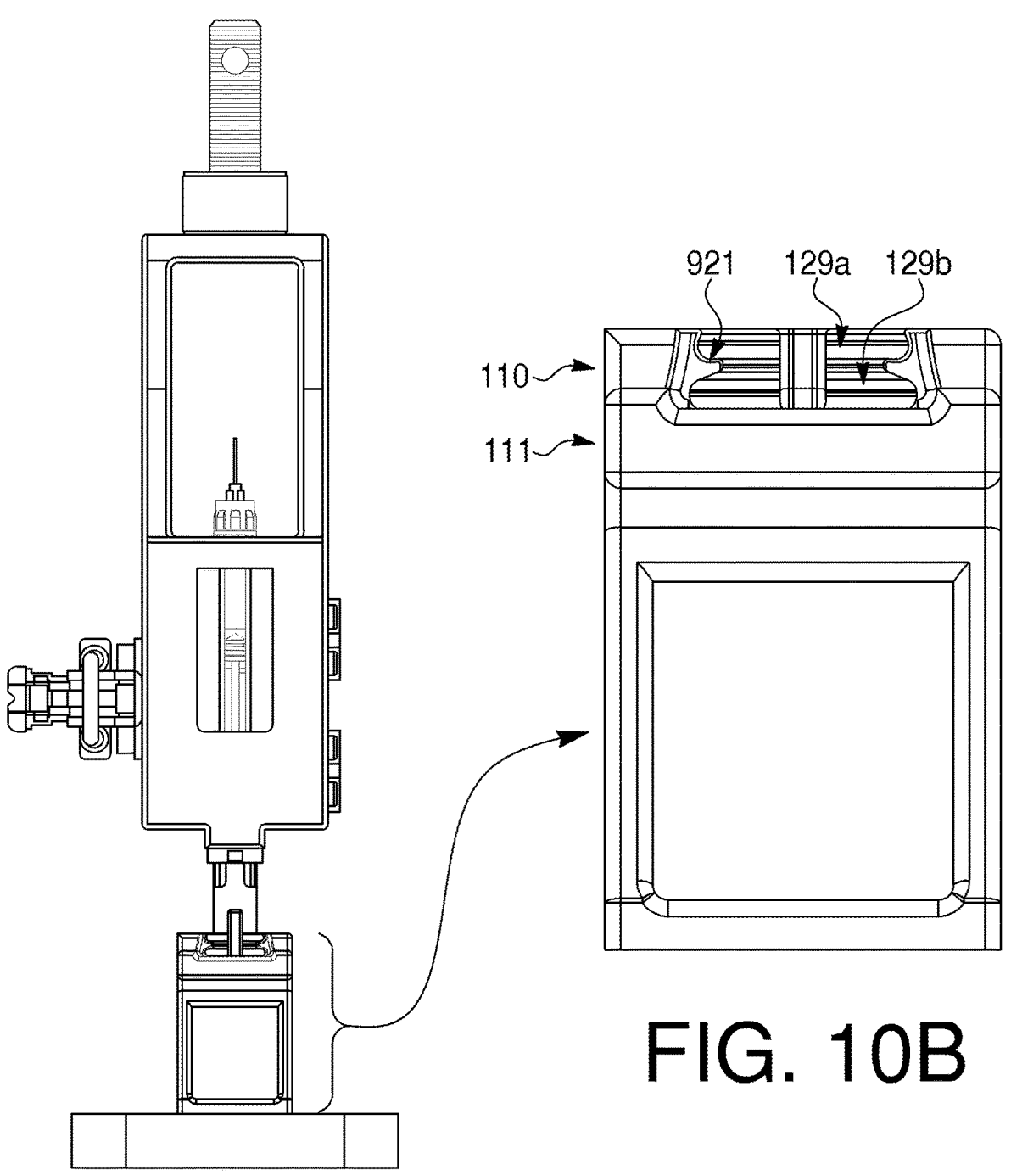
Figure 10D:
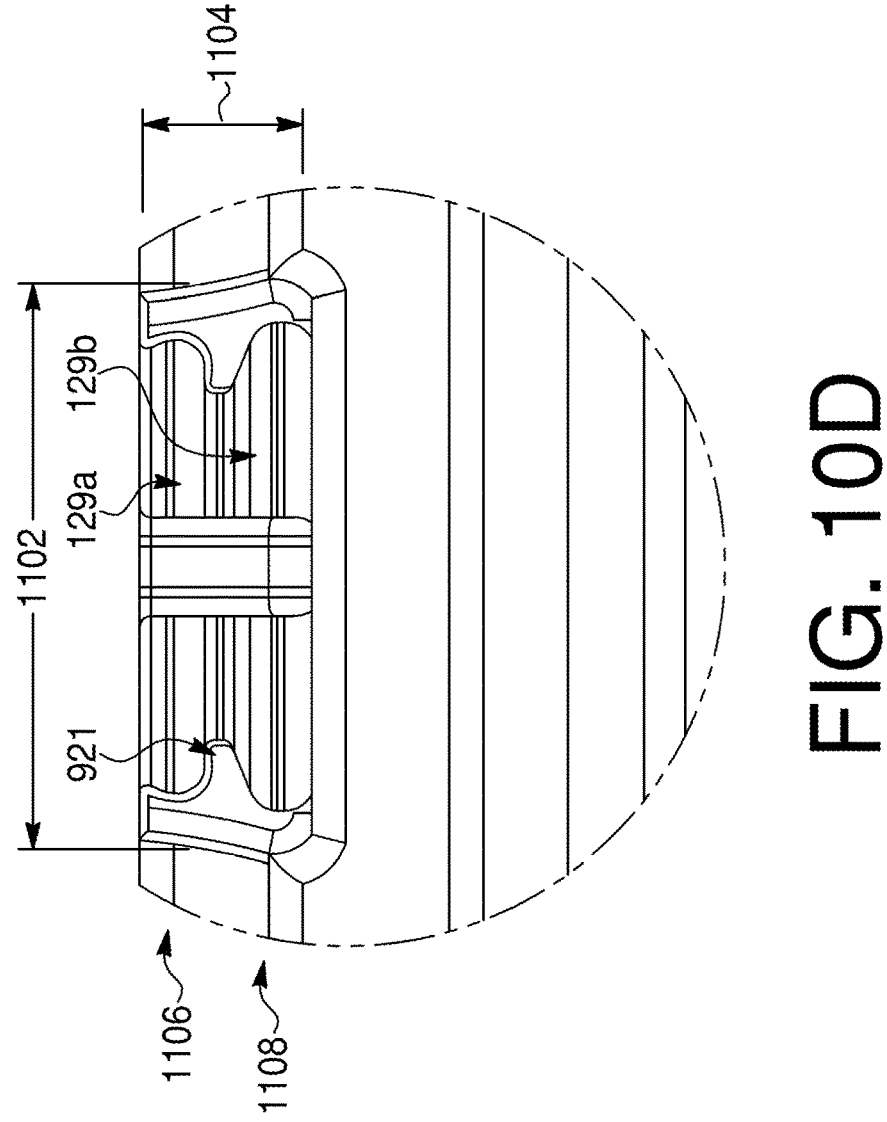
Figure 10C:
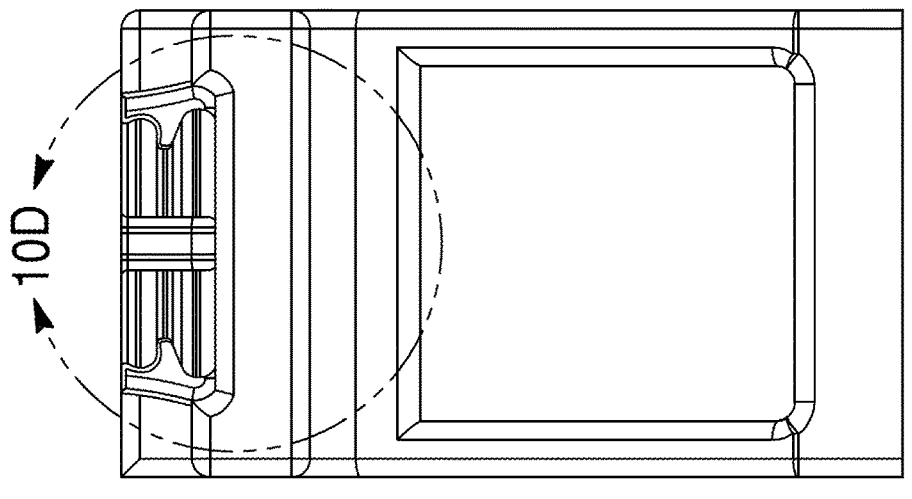

FIGS. 10A-10D show holder 111 with plunger top 119 inserted. FIG. 10D shows various measurements in reference of plunger top 119 inserted in holder 111. The widest diameter 1102 in holder 111 corresponds to the widest diameter 1010 of casing 110 and may range from about 16.50 mm to about 17.50 mm, about 16.55 mm to about 17.40 mm, about 16.60 mm to about 17.30 mm, about 16.60 mm to about 17.20 mm, about 16.60 mm to about 17.10 mm, about 16.62 to about 17.02, about 16.72 mm to about 16.92 mm, or about 16.82 mm. In some examples, the diameter ranges from about 16.62 mm to about 17.02 mm or 16.82 mm±0.20 mm.

The height of the top portion 916 of holder 111, represented by 1104 in FIG. 10D, that secures plunger top 119 may range from about 4.50 mm to about 5.50 mm, about 4.60 mm to about 5.40 mm, about 4.70 mm to about 5.30 mm, about 4.80 mm to about 5.20 mm, about 4.90 mm to about 5.20 mm, about 4.92 mm to about 5.12 mm, or about 5.02 mm. In some examples, the height ranges from about 4.92 mm to about 5.12 mm or 5.02 mm+0.10 mm.

When syringe 105 is installed onto holder 111, holding portion 921 fits in between first ring 129a and second ring 129b of plunger top 119. The height of first ring 129a that is encased in holder 111 is shown as 1106 in FIG. 10D and can range from about 2.00 mm to about 3.00 mm, about 2.05 mm to about 2.50 mm, about 2.10 mm to about 2.45 mm, about 2.15 mm to about 2.40 mm, about 2.17 mm to about 2.37 mm, or about 2.27 mm. In some examples, the height ranges from about 2.17 mm to about 2.37 mm or 2.27±0.10 mm. In addition, the height of second ring 129b that is encased in holder 111 is shown as 1108 in FIG. 10D and can range from about 2.00 mm to about 3.00 mm, about 2.10 mm to about 2.90 mm, about 2.20 mm to about 2.80 mm, about 2.30 mm to about 2.60 mm, about 2.36 mm to about 2.56 mm, or about 2.46 mm. In some examples, the height may range from 2.36 mm to about 2.56 mm, or about 2.46 mm±0.10 mm.

Casing 110 may be placed on top of or in line with and encasing a portion of holder 111. A fastener 114 may be inserted into one or both of casing 110 and holder 111 to encase and securely hold plunger top 119. Fastener 114 may be a key, rod, pin, or any appropriate means to lock casing 110 and holder 111 together.

Referring to FIGS. 11A-11F, casing 110 may have a plurality of sidewalls 1002a, 1002b, 1002c, a top wall 1004, and a second holding area 1001 configured to surround a portion of plunger top 119. When casing 110 is attached to holder 111 using a fastener 114, holding portion 921 of holder 111 and second holding area 1001 of casing 110 may securely hold plunger top 119 within base portion 130. One or more of the plurality of sidewalls 1002a, 1002b, 1002c, may include a through hole configured to receive fastener 114. Top wall 1004 may have a configuration corresponding to holder 111, such that casing 110 and holder 111 together may form a secure hold of plunger top 119. In some examples, top wall 1004 may include a notch 1006. A portion of plunger top 119, e.g., a protrusion 131, may fit into notch 1006 to securely hold plunger top 119. The configuration of notch 1006 may be complimentary to notch 924, such that notch 1006 and notch 924 may together securely hold plunger top 119. In other examples, the casing 110 and the holder 111 may contain any number of notches or protrusions to allow rotation of the syringe 105.

FIG. 11D shows various measurements of top wall 1004. For example, notch 1006 may have a width, represented as Q, ranging from about 2.50 mm to about 3.50 mm, about 2.70 mm to about 3.30 mm, about 2.70 mm to about 3.10 mm, about 2.80 mm to about 3.00 mm, or about 2.90 mm. In some examples, notch 1006 has a width ranging from about 2.70 mm to about 3.10 mm or 2.90±0.20 mm. Additional measurements of top wall 1004 may be made in reference to an inner circumference 1008. Top wall 1004 may include a plurality of shoulder portions 1007a, 1007b wherein a distance from an outer edge of either shoulder portion 1007a, 1007b to inner circumference 1008, represented as T, ranges from about 2.00 mm to about 3.00 mm, about 2.14 mm to about 2.94 mm, about 2.24 mm to about 2.84 mm, about 2.34 mm to about 2.54 mm, or about 2.44 mm. In some examples, the distance from an outer edge of either shoulder portion 1007a, 1007b to inner circumference 1008 ranges from about 2.34 mm to about 2.54 mm or 2.44 mm±0.10 mm. A distance from a top edge of either shoulder portion 1007a, 1007b to a central axis of inner circumference 1008, represented as S, ranges from about 1.00 mm to about 2.00 mm, about 1.15 mm to about 1.85 mm, about 1.25 mm to about 1.65 mm, about 1.35 mm to about 1.55 mm, or about 1.45 mm. In some examples, the distance from the top edge of either shoulder portion 1007a, 1007b to a central axis of inner circumference 1008 ranges from about 1.25 mm to about 1.65 mm or 1.45 mm±0.20 mm. A top edge of notch 1006 to inner circumference 1008, represented as R, ranges from about 2.00 mm to about 3.00 mm, about 2.20 mm to about 2.80 mm, about 2.30 mm to about 2.60 mm, about 2.37 mm to about 2.57 mm, or about 2.47 mm. In some examples, the distance from top edge of notch 1006 to inner circumference 1008 ranges from about 2.37 mm to about 2.57 mm or 2.47 mm±0.10 mm.

FIG. 11F shows various measurements in reference to plunger top 119 inserted in the interior of casing 110. For example, the thickness of top wall 1004, represented as 1009, ranges from about 3.50 mm to about 4.00 mm, about 3.55 mm to about 3.95 mm, about 3.60 mm to about 3.90 mm, about 3.65 mm to about 3.85 mm, or about 3.75 mm. In some examples, the height of top wall 1004 ranges from about 3.65 mm to about 3.85 mm or 3.75±0.10 mm. In some examples, the portion of top wall 1004 configured to hold plunger top 119 may have a diameter 1010 ranging from about 16.50 mm to about 17.50 mm, about 16.55 mm to about 17.40 mm, about 16.60 mm to about 17.30 mm, about 16.60 mm to about 17.20 mm, about 16.60 mm to about 17.10 mm, about 16.62 to about 17.02, about 16.72 mm to about 16.92 mm, or about 16.82 mm. In some examples, the diameter may range from about 16.62 mm to about 17.02 mm or 16.82 mm±0.20 mm.

When casing 110 is installed onto holder 111 and encases plunger top 119, second holding area 1001 fits in between first ring 129a and second ring 129b of plunger top 119. The height of first ring 129a that is encased in casing 110 is shown as 1011 in FIG. 11F and can range from about 1.00 mm to about 3.00 mm, about 2.00 mm to about 3.00 mm, about 2.12 mm to about 2.32 mm, or about 2.22 mm. In some examples, the height 1011 ranges from about 2.12 mm to about 2.32 mm or 2.22 mm 10.10 mm. In addition, the height of second ring 129b that is encased in casing 110 is shown as 1012 in FIG. 11F and can range from about 1.00 mm to about 2.00 mm, about 1.10 mm to about 1.30 mm, about 1.15 mm to about 1.25 mm, or about 1.252 mm. In some examples, the height 1012 ranges from about 1.15 mm to about 1.35 mm or 1.25 mm±0.10 mm.

When the flange 117 and plunger top 119 are properly secured in the second chamber 124 and base portion 130, respectively, syringe 105 may extend from base portion 130, through second chamber 124, and into first chamber 122. In some examples, at least the needle and needle cap portions 115 of syringe 105 may be received in first chamber 122 and top opening portion 134a. Top opening portion 134a may have a height, represented as C in FIG. 4C, ranging from about 60 mm to about 70 mm. For example, the height of top opening portion 134a may range from about 60 mm to about 68 mm, about 60 mm to about 66 mm, about 62 mm to about 70 mm, about 62 mm to about 68 mm, about 62 mm to about 66 mm, about 64 mm to about 66 mm, or about 65.00 mm. In some examples, the height of top opening portion 134a ranges from about 64.00 mm to about 66.00 mm or 65.00 mm+1.00 mm. The height of top opening portion 134a may be chosen so as to provide enough clearance, i.e., space, such that a user may prime the syringe, e.g., by removing the needle cap and/or inserting a needle into the syringe, without disturbing the alignment of the syringe while it is held in syringe fixture 100. In some examples, the height of top opening portion 134a may be chosen to provide enough space that a fully assembled syringe with a needle can be loaded into the fixture.

In some examples, the portions of syringe 105 in first chamber 122 and top opening portion 134a may not be attached to any component of syringe fixture 100. In such a configuration, syringe 105 may be securely held in syringe fixture 100 via a second chamber 124 and base portion 130.

Referring now to the additional embodiments of FIGS. 12A-12E, base portion 130 may include a lug 1200, a thumb nut 1210, connector 1220, and support 112. As shown in FIG. 12A, lug 1200 may be configured to hold a portion of plunger rod 128 and connector 1220 may be configured to attach to support 112. With specific reference to FIG. 12B, lug 1200 may include a first end 1201 and a second end 1202, and a circumferential sidewall 1204 which may extend from first end 1201 to second end 1202. In some embodiments, sidewall 1204 may flare away from first end 1201. In some embodiments, for example FIG. 12B, sidewall 1204 may form a rounded or circular shape, wherein sidewall 1204 extends from and flares away from first end 1201. Sidewall 1204 may flare away from first end 1201 at an angle ranging from about 90° to about 102°, about 91° to about 101°, about 92° to about 100°, about 93° to about 99°, about 94° to about 98°, or about 95° to about 97°. Sidewall 1204 may flare away from first end 1201 at an angle of about 90°, about 91°, about 92°, about 93°, about 94°, about 95°, about 96°, about 97°, about 98°, about 99°, about 100°, about 101°, or about 102°.

As shown in FIG. 12B, lug 1200 may include a plurality of ridges 1206 that extend inwardly from sidewall 1204 and towards the center of lug 1200. Ridges 1206 may have any shape and configuration suitable for engaging with a portion of plunger rod 128 (FIG. 14). In some examples, ridges 1206 may each have a substantially rectangular cross-sectional shape, as shown in FIGS. 12B, 12D, 12E, 13B, and 14. As shown in FIG. 12B, lug 1200 may include an interior wall 1203. Interior wall 1203 may include a fastener hole 1207 for receiving a fastening means 1208, e.g., a screw. Lug 1200 may be attached to other portions of base portion 130 by any appropriate fastening means 1208, e.g., a screw.

With continuing reference to FIG. 12B, connector 1220 may be attached to lug 1200, such that connector 1220 extends from first end 1201 of lug 1200. Connector 1220 may have a substantially cylindrical shape, wherein connector 1220 extends from first end 1201 of lug 1200 and connects to support 112. As shown in FIGS. 12A-12C, connector 1220 may include an opening 1222 for receiving a connector fastener 1224, e.g., a screw or a pin. In some embodiments, connector 1220 may include a plurality of openings 1222 and a plurality of connector fasteners 1224. As shown in FIG. 12C, thumb nut 1210 may surround a portion of lug 1200 and/or a portion of connector 1220 in order to connect and/or secure lug 1200 and/or connector 1220 to the mechanical test system. Thumb nut 1210 may include a recess portion 1212. In some embodiments, thumb nut 1210 may include a plurality of recess portions 1212. In some embodiments, recess portions 1212 may be configured to receive a tightening means, e.g., a tightening bar or a screw, to tighten thumb nut 1210.

Referring now to FIG. 12E, each ridge 1206a, 1206b, 1206c, and 1206d may be configured in lug 1200 such that each lug is equidistant from another ridge. A distance between ridge 1206a and 1206b, represented by M1, may range from about 14.10 mm to about 15.10 mm, about 14.20 mm to about 15.10 mm, about 14.30 mm to about 14.90 mm, about 14.40 mm to about 14.80 mm, or about 14.50 mm to about 14.70 mm. In some examples, the distance between ridge 1206a and 1206b may be about 14.10 mm, about 14.20 mm, about 14.30 mm, about 14.40 mm, about 14.50 mm, about 14.60 mm, about 14.70 mm, about 14.80 mm, about 14.90 mm, about 15.00 mm, or about 15.10 mm. An internal radius of curvature of lug 1200, represented as R1 in FIG. 12E, may be R8, R9, R10, R11, or R12.

Referring to FIGS. 12E and 13B, fastener hole 1207 may have a diameter ranging from about 7.93 mm to about 8.93 mm, about 8.03 mm to about 8.83 mm, about 8.13 mm to about 8.73 mm, about 8.23 mm to about 8.63 mm, or about 8.33 mm to about 8.53 mm. In some examples, the diameter of fastener hole 1207 may be about 7.93 mm, about 8.03 mm, about 8.13 mm, about 8.23 mm, about 8.33 mm, about 8.43 mm, about 8.53 mm, about 8.63 mm, about 8.73 mm, about 8.83 mm, or about 8.93 mm. In some examples, a countersink angle (not shown) of fastener hole 1207 may range from about 80° to about 120° or about 90° to about 110°. The countersink angle may be about 80°, about 82°, about 90°, about 100°, about 110°, or about 120°.

Referring to FIG. 12E, fastening means 1208 may have a diameter ranging from about 4.00 mm to about 5.00 mm, about 4.10 mm to about 4.90 mm, about 4.20 mm to about 4.80 mm, about 4.30 mm to about 4.70 mm, or about 4.40 mm to about 4.60 mm. In some examples, the diameter of fastening means 1208 may be about 4.00 mm, about 4.10 mm, about 4.20 mm, about 4.30 mm, about 4.40 mm, about 4.50 mm, about 4.60 mm, about 4.70 mm, about 4.80 mm, about 4.90 mm, or about 5.00 mm.

Referring to FIG. 13A, a distance between first end 1201 and second end 1202 of lug 1200, represented by M4, may range from about 13.5 mm to about 14.5 mm, about 13.6 mm to about 14.4 mm, about 13.7 mm to about 14.3 mm, about 13.8 mm to about 14.2 mm, or about 13.9 mm to about 14.1 mm. In some examples, the distance between first end 1201 and second end 1202 may be about 13.5 mm, about 13.6 mm, about 13.7 mm, about 13.8 mm, about 13.9 mm, about 14 mm, about 14.1 mm, about 14.2 mm, about 14.3 mm, about 14.4 mm, or about 14.5 mm.

A diameter of lug 1200 at first end 1201, represented by M2, may range from about 23.71 mm to about 24.71 mm, about 23.81 mm to about 24.61 mm, about 23.91 mm to about 24.51 mm, about 24.01 mm to about 24.41 mm, or about 24.11 mm to about 24.31 mm. In some examples, a diameter of lug 1200 at first end 1201 may be about 23.71 mm, about 23.81 mm, about 23.91 mm, about 24.01 mm, about 24.41 mm, about 24.11 mm, about 24.21 mm, about 24.31 mm, about 24.41 mm, about 24.51 mm, about 24.61 mm, or about 24.71 mm. A diameter of lug 1200 at second end 1202, represented by M3, may range from about 26.65 mm to about 27.65 mm, about 26.75 mm to about 27.55 mm, about 26.85 mm to about 27.45 mm, about 26.95 mm to about 27.35 mm, or about 27.05 mm to about 27.25 mm. In some examples, A diameter of lug 1200 at second end 1202 may be about 26.65 mm, about 26.75 mm, about 26.85 mm, about 26.95 mm, about 27.05 mm, about 27.15 mm, about 27.25 mm, about 27.35 mm, about 27.45 mm, about 27.55 mm, or about 27.65 mm. In some embodiments, a diameter of second end 1202 may be larger than a diameter of first end 1201. In some examples, lug 1200 may have a radius of curvature, represented as R2 in FIG. 13A, of R0.10, R0.20, R0.30, R0.40, or R0.50.

FIG. 13B is a cross-sectional view along line E-E of FIG. 12E. As depicted, a height of ridge 1206, represented by M5, may range from about 8.5 mm to about 9.5 mm, about 8.6 mm to about 9.4 mm, about 8.7 mm to about 9.3 mm, about 8.8 mm to about 9.2 mm, or about 8.9 mm to about 9.1 mm. In some examples, a height M5 of ridge 1206 may be about 8.5 mm, about 8.6 mm, about 8.7 mm, about 8.8 mm, about 8.9 mm, about 9 mm, about 9.1 mm, about 9.2 mm, about 9.3 mm, about 9.4 mm, or about 9.5 mm. A width of ridge 1206, represented by M6, may range from about 2.32 mm to about 3.32, about 2.42 mm to about 3.22 mm, about 2.52 mm to about 3.12 mm, about 2.62 mm to about 3.02 mm, or about 2.72 mm to about 2.92 mm. In some examples, the width M6 of ridge 1206 may be about 2.32 mm, about 2.42 mm, about 2.52 mm, about 2.62 mm, about 2.72 mm, about 2.82 mm, about 2.92 mm, about 3.02 mm, about 3.12 mm, about 3.22 mm, or about 3.32 mm.

As mentioned above, FIG. 14 depicts how a portion of plunger rod 128, for example, plunger top 119 and/or protrusions 131, may fit into lug 1200. Referring to the arrows, protrusions 131 of plunger top 119 may fit in between at least two ridges 1206. At least two ridges 1206 may be spaced on either side of protrusions 131 in order to securely capture plunger top 119 to lug 1200. In some embodiments, where plunger top 119 includes more than one protrusion 131, each protrusion 131 may fit in between at least two ridges 1206.

As those of ordinary skill in the art will readily recognize, as lug 1200 is rotated (e.g., clockwise or counterclockwise)

about a longitudinal axis, side walls of ridges 1206 will move into contact with side walls of protrusions 131, thereby imparting a similar rotational motion on plunger 109.

In some embodiments, syringe fixture 100 may be secured to a mechanical test system, e.g., an Instron® test system. For attachment to a test system, one of the second plurality of walls 152a, 152b may include an attachment means. For example, wall 152a may include a fastener 102, e.g., a screw. Fastener 102 may be attached to wall 152a via a nut or clamp 103. In other examples, fastener 102 may include a through hole 101 for further attachment to the testing system. For further attachment to a test system, support 112 of base portion 130 may include various screw holes (FIG. 3) configured to receive fasteners, e.g., screws or bolts, to secure support 112 of syringe fixture 100 to the test system. Mechanical test systems, e.g., an Instron® test system, may include a movable portion and a stationary portion. In some systems, the movable portion may be superior to, i.e., above, the stationary portion, such that the movable portion and stationary portion are in coaxial alignment.

As described above, syringe 105 may include a needle and needle cap portion 115, which may also be referred to herein as the "needle end", and syringe plunger end 109, which may also be referred to herein as the "plunger end." Referring to syringe 105, syringe fixture 100 may be configured such that fastener 102 is superior to the needle end and base portion 130 inferior to the plunger end, e.g., as shown in FIG. 1A. The configuration of syringe fixture 100 in FIG. 1A may be used in a mechanical test system as described above such that fastener 102 attaches to the movable portion and base portion 130 attaches to the stationary portion. In alternative embodiments, syringe fixture 100 may be configured such that base portion 130 is superior to the plunger end and fastener 102 is inferior to the needle end, e.g., as shown in FIG. 15. The configuration of syringe fixture 100 in FIG. 15 may be used in a mechanical test system as described above such that base portion 130 attaches to the movable portion and fastener 102 attaches to the stationary portion.

For purposes of discussion herein, the configuration of syringe fixture 100 in FIG. 1A will be referred to as "needle up", i.e., the needle points upwards, and the configuration of syringe fixture 100 in FIG. 15 will be referred to as "needle down", i.e., the needle points downwards. Whichever orientation is used, may depend on the mechanical test system and/or the type of mechanical test performed. Various mechanical tests that may be performed using syringe fixture 100 include maximum injection force, use torque, override torque, full injection force, and priming. For example, a maximum injection force test may be performed with the needle down, such that the contents of the syringe may be fully expelled during the test, leveraging the forces of gravity. A test to measure use torque may be performed with the needle down, so that a plunger rod of the syringe may rotate. A test to measure override torque, i.e., how much force is needed to overcome the initial friction forces between the syringe's stopper and sidewall when expelling the contents of the syringe may also be performed in a configuration with the needle pointing downwards. To measure a full injection force profile of the syringe, the syringe fixture 100 may be in the needle up position. In addition, testing the priming of the syringe may also be done in the needle up position. None of the tests discussed above or that may be done with syringe fixture 100 are limited to the needle up or needle down configurations.

EXAMPLE

The following example is provided for illustration purposes only and is not intended to limit any single aspect or embodiment of the syringe fixture, nor is it limited to any combinations and/or permutations of such aspects and/or embodiments. This example illustrates how the syringe fixture of the present disclosure can be used with a dose precision system syringe that is described in WO 2019/118588 or WO 2020/247686. A person skilled in the art would appreciate that the syringe fixture can be adapted to fit other types of syringes and that other measurements are possible given various applications and/or medicaments disposed within the syringe.

An exemplary use of syringe fixture embodiments as disclosed is provided herein. A syringe fixture was inserted into and attached an Instron® test system, such that the first chamber is on top, e.g., as shown in FIG. 1A. The needle cap of a dose precision system syringe of interest (as described in WO 2019/118588 or WO 2020/247686) was removed and a hypoint needle, along with its needle cover, was attached to the exposed needle end of the syringe. The needle was rotated onto the syringe via a luer connection until there was resistance and the needle felt secure within the luer adaptor of the syringe. The handle on the second chamber was then unlocked, so that the cover may be opened. The prepared syringe was placed into the syringe fixture, such that the flange and flange body was contained in the second chamber and the syringe body and needle end extended through the second chamber and into the first chamber. The cover was then moved to enclose and secure the flange and flange body of the syringe and the handle was locked. A program for the Instron® test system was initiated and all of the steps discussed above were repeated for four samples. The injection force profiles were analyzed for each of the four samples. The results of the injection force profiles is provided in FIG. 16. As illustrated, the first force was the break force followed by a snap deflection force when the snap tabs of the plunger rod were moved from the windows/slots of the flange. Once the snaps were deflected, the plunger rod continued to depress the piston to remove the air within the system, referred to as air glide force. Once the piston contacted the fluid, it was expelled as shown in the fluid priming glide force. The fluid dosing glide force illustrated in FIG. 16 represents the dosing force after the plunger rod was rotated.

FIG. 17 summarizes the mean and standard deviations for the forces for all samples, and the histogram in FIG. 18 graphically represents the data for maximum injection force.

As illustrated in FIG. 19, the torque of the plunger rod was measured during the 90-degree rotation of the plunger rod. The maximum torque force occurred at the average rotation of 61.8-degrees. The mean of the maximum torque was 21.28N*mm with a standard deviation of 1.916N*mm.

Testing was also performed using syringes with flanges made from polypropylene. The mean of the PP maximum torque is 23.854 N*mm with a standard deviation of 2.173 N*mm. The results are illustrated in FIGS. 20 and 21.

The description above and examples are illustrative and are not intended to be restrictive. One of ordinary skill in the art may make numerous modifications and/or changes without departing from the general scope of the invention. For example, and as has been referenced, aspects of above-described embodiments may be used in any suitable com-bination with each other. Additionally, portions of the above-described embodiments may be removed without departing from the scope of the invention. In addition, modifications may be made to adapt a particular situation or aspect to the teachings of the various embodiments without departing from their scope. Many other embodiments will also be apparent to those of skill in the art upon reviewing the above description.

Embodiments of the present disclosure may include the following features:

Item 1. A syringe fixture for holding a syringe in a test system, the fixture comprising:
a main housing comprising a first chamber, a second chamber, and an opening extending from the first chamber to the second chamber,
wherein the first chamber comprises a first plurality of walls having a first length and a second plurality of walls having a second length, wherein the second length is less than the first length, and the first and second pluralities of walls form a housing for at least a needle of the syringe, and
wherein the second chamber is configured to hold at least a flange portion of the syringe and the second chamber comprises a cover to enclose at least the flange portion of the syringe; and
a base portion having a support, wherein the base portion is configured to receive a portion of a plunger rod of the syringe, and wherein the base portion includes at least one geometric feature configured to allow or impart a rotational motion on the portion of the plunger rod received in the base portion.

Item 2. The syringe fixture of item 1, wherein the base portion includes a holder for a plunger rod of the syringe and a casing, wherein the casing and the holder are configured to be secured together via a fastener to support the plunger rod.

Item 3. The syringe fixture of item 1, wherein the base portion includes a lug configured to receive a plunger rod of the syringe and a connector, wherein the lug and connector are secured together to support the plunger rod.

Item 4. The syringe fixture of item 1, wherein the second chamber is removable from the main housing.

Item 5. The syringe fixture of item 4, wherein the second chamber has a first configuration and is interchangeable with a different second chamber having a second configuration, wherein the second configuration is different from the first configuration.

Item 6. The syringe fixture of item 1, wherein the second plurality of walls includes a top wall and a bottom wall, the top wall comprising a fastener for securing the main housing to the test system.

Item 7. The syringe fixture of item 1, wherein the support of the base portion includes screw holes for securing the base to the test system.

Item 8. The syringe fixture of item1, wherein the cover is attached to the second chamber via hinges and a closure, the closure configured to allow for opening and closing of the cover.

Item 9. The syringe fixture of item 1, wherein the second chamber includes a chamber extension extending from a bottom section of the second chamber and the cover includes a cover extension extending from a bottom section of the cover, wherein each portion has a height ranging from about 4.80 mm to about 5.20 mm.

Item 10. The syringe fixture of item 7, wherein each of the chamber extension of the second chamber and the cover extension of the cover has a length ranging from about 13.22 mm to about 13.62 mm.

Item 11. The syringe fixture of item 7, wherein a clearance between the chamber extension of the second chamber and the cover extension of the cover ranges from about 12.95 mm to about 13.35 mm.

Item 12. The syringe fixture of item 1, wherein the first chamber of the main housing is configured to be secured to a movable portion of the test system and the support of the base portion is configured to be secured to a stationary portion of the test system.

Item 13. The syringe fixture of item 1, wherein the first chamber of the main housing is configured to be secured to a stationary portion of the test system and the support of the base portion is configured to be secured to a movable portion of the test system.

Item 14. A syringe fixture for holding a syringe in a test system, the fixture comprising:

a main housing comprising a first chamber, a second chamber, and an opening extending from the first chamber to the second chamber, wherein the first chamber comprises a housing for at least a needle of the syringe, and wherein the second chamber is configured to receive at least a flange portion of the syringe and the second chamber comprises a cover to enclose at least the flange portion of the syringe; and a base portion having a support, wherein the base portion includes a lug configured to receive a plunger rod of the syringe, and a connector, wherein the lug and connector are secured together to support the plunger rod.

Item 15. The syringe fixture of item 14, wherein the base portion includes a thumb nut to secure and stabilize the lug and connector to the test system.

Item 16. The syringe fixture of item 14, wherein the lug includes an opening for receiving a portion of the plunger rod, and wherein the opening includes a plurality of ridges configured to engage with a portion of the plunger rod.

Item 17. The syringe fixture of item 16, wherein the lug includes a first end having a first diameter and a second end having a second diameter, wherein the second diameter is larger than the first diameter, and a sidewall extending from the first end to the second end, wherein the sidewall flares outwardly from the first end to the second end.

Item 18. A method for testing a syringe, the method comprising:

securing a syringe fixture to a test system, the fixture comprising:

a main housing comprising a first chamber, a second chamber, and an opening extending from the first chamber to the second chamber, wherein the first chamber comprises a housing for at least a needle and a needle cap of the syringe, and wherein the second chamber is configured to hold at least a flange portion of the syringe and the second chamber comprises a cover to enclose at least the flange portion of the syringe; and a base portion having a support, and inserting the syringe into the syringe fixture.

Item 19. The method of item 18, further comprising securing the first chamber of the main housing to a movable portion of the test system and securing the support of the base portion to a stationary portion of the test system.

Item 20. The method of item 18, further comprising securing the first chamber of the main housing to a stationary portion of the test system and securing the support of the base portion to a movable portion of the test system.

What is claimed is:

1. A syringe fixture for holding a syringe in a test system, the fixture comprising:

a main housing comprising a first chamber, a second chamber, and an opening extending from the first chamber to the second chamber, wherein the first chamber comprises a first plurality of walls having a first length and a second plurality of walls having a second length, wherein the second length is less than the first length, and the first and second pluralities of walls form a housing for at least a needle of the syringe, and wherein the second chamber is positioned below the first chamber and configured to hold at least a flange portion of the syringe, such that the main housing is configured to hold the needle relatively above the flange portion, and the second chamber comprises a cover to enclose at least the flange portion of the syringe; and a base portion having a support, wherein the base portion is configured to receive a portion of a plunger rod of the syringe, and wherein the base portion includes at least one geometric feature configured to allow or impart a rotational motion on the portion of the plunger rod received in the base portion.

2. The syringe fixture of claim 1, wherein the base portion includes a holder for the plunger rod of the syringe and a casing, wherein the casing and the holder are configured to be secured together via a fastener to support the plunger rod.

3. The syringe fixture of claim 1, wherein the base portion includes a lug configured to receive the plunger rod of the syringe and a connector, wherein the lug and the connector are secured together to support the plunger rod.

4. The syringe fixture of claim 1, wherein the second chamber is removable from the main housing.

5. The syringe fixture of claim 4, wherein the second chamber has a first configuration and is interchangeable with a different second chamber having a second configuration, wherein the second configuration is different from the first configuration.

6. The syringe fixture of claim 1, wherein the second plurality of walls includes a top wall and a bottom wall, the top wall comprising a fastener for securing the main housing to the test system.

7. The syringe fixture of claim 1, wherein the support of the base portion includes screw holes for securing the base portion to the test system.

8. The syringe fixture of claim 1, wherein the cover is removable from the main housing and configured to be selectively attached to the main housing below the first chamber and laterally along the second chamber.

9. The syringe fixture of claim 1, wherein the second chamber includes a chamber extension extending from a bottom section of the second chamber and the cover includes a cover extension extending from a bottom section of the cover, wherein each portion has a height ranging from about 4.80 mm to about 5.20 mm.

10. The syringe fixture of claim 9, wherein each of the chamber extension of the second chamber and the cover extension of the cover has a length ranging from about 13.22 mm to about 13.62 mm.

11. The syringe fixture of claim 9, wherein a clearance between the chamber extension of the second chamber and the cover extension of the cover ranges from about 12.95 mm to about 13.35 mm.

12. The syringe fixture of claim 1, wherein the first chamber of the main housing is configured to be secured to a movable portion of the test system and the support of the base portion is configured to be secured to a stationary portion of the test system.

13. The syringe fixture of claim 1, wherein the first chamber of the main housing is configured to be secured to a stationary portion of the test system and the support of the base portion is configured to be secured to a movable portion of the test system.

14. A syringe fixture for holding a syringe in a test system, the fixture comprising:

a main housing comprising a first chamber, a second chamber, and an opening extending from the first chamber to the second chamber, wherein the first chamber comprises a housing for at least a needle of the syringe, and wherein the second chamber is configured to receive at least a flange portion of the syringe and the second chamber comprises a removable cover that is configured to couple onto an exterior sidewall of the main housing along the second chamber to enclose at least the flange portion of the syringe; and a base portion having a support, wherein the base portion includes a lug configured to receive a plunger rod of the syringe, a connector, wherein the lug and the connector are secured together to support the plunger rod.

15. The syringe fixture of claim 14, wherein the base portion includes a thumb nut for securing and stabilizing the lug and the connector to the test system.

16. The syringe fixture of claim 14, wherein the lug includes an opening for receiving a portion of the plunger rod, and wherein the opening includes a plurality of ridges configured to engage with the portion of the plunger rod.

17. The syringe fixture of claim 16, wherein the lug includes a first end having a first diameter and a second end having a second diameter, wherein the second diameter is larger than the first diameter, and a sidewall extending from the first end to the second end, wherein the sidewall flares outwardly from the first end to the second end.

18. A method for testing a syringe, the method comprising:

securing a syringe fixture to a test system, the syringe fixture comprising:

a main housing comprising a first chamber, a second chamber, and an opening extending from the first chamber to the second chamber, wherein the first chamber comprises a housing for at least a needle and a needle cap of the syringe, and wherein the second chamber is configured to hold at least a flange portion of the syringe and the second chamber comprises a cover to enclose at least the flange portion of the syringe; and a base portion having a support, the base portion is separated from the main housing such that a gap defining a clearance is positioned between the base portion and the main housing; and inserting the syringe into the syringe fixture with at least a plunger rod portion of the syringe disposed within the gap, such that the plunger rod portion is held outside of the main housing and the base portion.

19. The method of claim 18, further comprising securing the first chamber of the main housing to a movable portion of the test system and securing the support of the base portion to a stationary portion of the test system.

20. The method of claim 18, further comprising securing the first chamber of the main housing to a stationary portion of the test system and securing the support of the base portion to a movable portion of the test system.

* * * * *